US008298147B2

(12) United States Patent
Huennekens et al.

(10) Patent No.: US 8,298,147 B2
(45) Date of Patent: Oct. 30, 2012

(54) THREE DIMENSIONAL CO-REGISTRATION FOR INTRAVASCULAR DIAGNOSIS AND THERAPY

(75) Inventors: Richard Scott Huennekens, San Diego, CA (US); Vincent J. Burgess, San Diego, CA (US); Marja Pauliina Margolis, Coral Gables, FL (US); Blair D. Walker, Mission Viejo, CA (US); Jon D. Klingensmith, El Dorado Hills, CA (US); Nancy Perry Pool, El Dorado Hills, CA (US); Randall Kent Hanson, Sacramento, CA (US)

(73) Assignee: Volcano Corporation, Rancho Cordova, CA (US)

( * ) Notice: Subject to any disclaimer, the term of this patent is extended or adjusted under 35 U.S.C. 154(b) by 891 days.

(21) Appl. No.: 11/473,974

(22) Filed: Jun. 23, 2006

(65) Prior Publication Data
US 2007/0038061 A1     Feb. 15, 2007

Related U.S. Application Data

(60) Provisional application No. 60/694,014, filed on Jun. 24, 2005.

(51) Int. Cl.
    *A61B 8/00*     (2006.01)
(52) U.S. Cl. ........ 600/443; 600/444; 600/463; 600/466; 600/467; 382/128; 382/130; 382/131
(58) Field of Classification Search .................. 600/427, 600/458, 437, 463, 466, 467; 623/1.42, 1.43; 382/130, 128, 131
See application file for complete search history.

(56) References Cited

U.S. PATENT DOCUMENTS

| 4,173,228 A | 11/1979 | Van Steenwyk |
| 4,821,731 A | 4/1989 | Martinelli |
| 4,838,879 A | 6/1989 | Tanabe |

(Continued)

FOREIGN PATENT DOCUMENTS

CA     2 449 080 A1     5/2005

(Continued)

OTHER PUBLICATIONS

"3D heart modelling from biplane, rotational angiocardiographic x-ray sequence" Kehl et al, Computer & Graphics 24 (2000), pp. 731-739.*

(Continued)

*Primary Examiner* — Brian Casler
*Assistant Examiner* — Joseph M Santos
(74) *Attorney, Agent, or Firm* — Haynes and Bone, LLP

(57) ABSTRACT

A method and system are disclosed for creating, in a coordinated manner, graphical images of a body including vascular features from a combination of image data sources. The method includes initially creating an angiographic image of a vessel segment. The angiographic image is, for example, either a two or three dimensional image representation. Next, a vessel image data set is acquired that is distinct from the angiographic image data. The vessel image data set comprises information acquired at a series of positions along the vessel segment. An example of such vessel image data is a set of intravascular ultrasound frames corresponding to circumferential cross-section slices taken at various positions along the vessel segment. The angiographic image and the vessel image data set are correlated by comparing a characteristic rendered independently from both the angiographic image and the vessel image data at positions along the vessel segment.

27 Claims, 24 Drawing Sheets

U.S. PATENT DOCUMENTS

| | | | |
|---|---|---|---|
| 4,875,165 A | 10/1989 | Fencil | |
| 4,938,220 A | 7/1990 | Mueller, Jr. | |
| 5,042,486 A | 8/1991 | Pfeiler | |
| 5,159,931 A | 11/1992 | Pini | |
| 5,175,773 A | 12/1992 | Garreau | |
| 5,203,777 A | 4/1993 | Lee | |
| 5,292,331 A * | 3/1994 | Boneau | 623/1.16 |
| 5,386,828 A | 2/1995 | Owens | |
| 5,429,617 A | 7/1995 | Hammersmark | |
| 5,485,840 A * | 1/1996 | Bauman | 600/439 |
| 5,540,229 A | 7/1996 | Coliet-Billon | |
| 5,592,939 A | 1/1997 | Martinelli | |
| 5,690,113 A | 11/1997 | Sliwa, Jr. | |
| 5,699,446 A | 12/1997 | Rougee | |
| 5,709,206 A | 1/1998 | Teboul | |
| 5,729,129 A | 3/1998 | Acker | |
| 5,744,953 A | 4/1998 | Hansen | |
| 5,752,513 A | 5/1998 | Acker | |
| 5,771,895 A | 6/1998 | Slager | |
| 5,824,042 A | 10/1998 | Lombardi | |
| 5,830,145 A | 11/1998 | Tenhoff | |
| 5,840,025 A | 11/1998 | Ben-Haim | |
| 5,872,861 A | 2/1999 | Makram-Ebeid | |
| 5,899,860 A | 5/1999 | Pfeiffer | |
| 5,921,978 A | 7/1999 | Thompson | |
| 5,954,647 A | 9/1999 | Bova | |
| 5,957,844 A | 9/1999 | Dekel | |
| 5,993,390 A | 11/1999 | Savord | |
| 6,014,473 A | 1/2000 | Hossack | |
| 6,016,439 A | 1/2000 | Acker | |
| 6,024,763 A | 2/2000 | Lenker | |
| 6,035,226 A | 3/2000 | Panescu | |
| 6,036,682 A | 3/2000 | Lange | |
| 6,083,167 A | 7/2000 | Fox | |
| 6,095,976 A | 8/2000 | Nachtomy | |
| 6,102,865 A | 8/2000 | Hossack | |
| 6,104,944 A | 8/2000 | Martinelli | |
| 6,132,376 A | 10/2000 | Hossack | |
| 6,148,095 A * | 11/2000 | Prause et al. | 382/131 |
| 6,152,878 A | 11/2000 | Nachtomy | |
| 6,159,225 A | 12/2000 | Makower | |
| 6,166,740 A | 12/2000 | Malzbender | |
| 6,190,353 B1 | 2/2001 | Makower | |
| 6,201,900 B1 | 3/2001 | Hossack | |
| 6,216,029 B1 | 4/2001 | Paltieli | |
| 6,233,476 B1 | 5/2001 | Strommer | |
| 6,246,898 B1 | 6/2001 | Vesely | |
| 6,248,075 B1 | 6/2001 | McGee | |
| 6,266,453 B1 * | 7/2001 | Hibbard et al. | 382/294 |
| 6,273,858 B1 | 8/2001 | Fox | |
| 6,275,724 B1 | 8/2001 | Dickinson | |
| 6,285,903 B1 | 9/2001 | Rosenthal | |
| 6,298,261 B1 | 10/2001 | Rex | |
| 6,314,310 B1 | 11/2001 | Ben-Haim | |
| 6,351,513 B1 | 2/2002 | Bani-Hashemi | |
| 6,360,027 B1 | 3/2002 | Hossack | |
| 6,374,134 B1 | 4/2002 | Bladen | |
| 6,389,104 B1 | 5/2002 | Bani-Hashemi | |
| 6,396,940 B1 * | 5/2002 | Carrott et al. | 382/128 |
| 6,405,072 B1 | 6/2002 | Cosman | |
| 6,501,848 B1 | 12/2002 | Carroll | |
| 6,515,657 B1 | 2/2003 | Zanelli | |
| 6,546,271 B1 | 4/2003 | Reisfeld | |
| 6,574,498 B1 | 6/2003 | Gilboa | |
| 6,577,889 B2 | 6/2003 | Ichihashi | |
| 6,612,992 B1 | 9/2003 | Hossack | |
| 6,638,222 B2 | 10/2003 | Chandrasekaran | |
| 6,650,927 B1 | 11/2003 | Keidar | |
| 6,673,018 B2 | 1/2004 | Friedman | |
| 6,695,779 B2 | 2/2004 | Sauer et al. | |
| 6,718,054 B1 | 4/2004 | Lorigo | |
| 6,719,700 B1 | 4/2004 | Willis | |
| 6,763,261 B2 | 7/2004 | Casscells, III et al. | |
| 6,775,404 B1 | 8/2004 | Pagoulatos | |
| 6,785,571 B2 | 8/2004 | Glossop | |
| 6,805,132 B2 | 10/2004 | Willis | |
| 6,831,644 B2 | 12/2004 | Lienard et al. | |
| 6,895,267 B2 | 5/2005 | Panescu et al. | |
| 6,896,657 B2 | 5/2005 | Willis | |
| 6,908,480 B2 | 6/2005 | Jayaraman et al. | |
| 6,923,768 B2 | 8/2005 | Camus et al. | |
| 6,970,733 B2 | 11/2005 | Willis | |
| 6,970,734 B2 | 11/2005 | Eidenschink et al. | |
| 6,980,675 B2 | 12/2005 | Evron et al. | |
| 7,035,371 B2 | 4/2006 | Boese et al. | |
| 2002/0019644 A1 | 2/2002 | Hastings | |
| 2002/0049375 A1 | 4/2002 | Strommer | |
| 2002/0099428 A1 | 7/2002 | Kaufman | |
| 2002/0115931 A1 * | 8/2002 | Strauss et al. | 600/420 |
| 2003/0078500 A1 | 4/2003 | Evron | |
| 2003/0139801 A1 * | 7/2003 | Sirhan et al. | 623/1.15 |
| 2003/0220555 A1 | 11/2003 | Heigl | |
| 2003/0231789 A1 | 12/2003 | Willis | |
| 2004/0102697 A1 | 5/2004 | Evron | |
| 2004/0114146 A1 | 6/2004 | Willis | |
| 2004/0138548 A1 | 7/2004 | Strommer | |
| 2005/0008210 A1 | 1/2005 | Evron | |
| 2005/0096647 A1 | 5/2005 | Steinke | |
| 2005/0113685 A1 | 5/2005 | Maschke | |
| 2005/0203369 A1 | 9/2005 | Sathyanarayana | |

FOREIGN PATENT DOCUMENTS

| | | |
|---|---|---|
| JP | 5064638 | 3/1993 |
| WO | WO 02/064011 A2 | 8/2002 |
| WO | WO-2004/075756 | 9/2004 |

OTHER PUBLICATIONS

No author, "Radiation Safety Manual for the Fluoroscopist", Internet source, 2000, Saint Luke's Hospital of Kansas City, Kansas City, U.S.A.

Bekeredjian, R., Hardt, S., Just, A., Hansen, A., Kuecherer, H., "Influence of Catheter Position and Equipment-Related Factors on the Accuracy of Intravascular Ultrasound Measurements", Journal of Invasive Cardiology, 1999, pp. 207-212, vol. 11, No. 4, Health Management Publications, King of Prussia, U.S.A.

Cavaye, D., Tabbara, M., Kopchok, G., Laas, T., White, R., "Three Dimensional Vascular Ultrasound Imaging", The American Surgeon, 1991, pp. 751-755, vol. 57, No. 12, Lippincott, Philadelphia, U.S.A.

Chen, S., Metz, C., "Improved Determination of Biplane Imaging Geometry from Two Projection Images and Its Application to Three-Dimensional Reconstruction of Coronary Trees", Medical Physics, 1997, pp. 633-654, vol. 24, No. 5, American Institute of Physics, New York, U.S.A.

Chen, S., Carroll, J., "3-D Reconstruction of Coronary Arterial Tree to Optimize Angiographic Visualization", IEEE Transactions on Medical Imaging, 2000, pp. 318-336, vol. 19, No. 4, Institute of Electrical and Electronics Engineers, New York, U.S.A.

Chen, S., Carroll, J., Messenger, J., "Quantitative Analysis of Reconstructed 3-D Coronary Arterial Tree and Intracoronary Devices", IEEE Transactions on Medical Imaging, 2002, pp. 724-740, vol. 21, No. 7, Institute of Electrical and Electronics Engineers, New York, U.S.A.

Cothren, R., Shekhar, R., Tuzcu, E., Nissen, S., Cornhill, J., Vince, D., "Three-Dimensional Reconstruction of the Coronary Artery Wall by Image Fusion of Intravascular ultrasound and Bi-Plane Angiography", International Journal of Cardiac Imaging, 2000, pp. 69-85, vol. 16, No. 2, Nijhoff, Boston, U.S.A.

Evans, J., NG, K., Wiet, S., Vonesh, M., Burns, W., Radvany, M., Kane, B., Davidson, C., Roth, S., Kramer, B., Meyers, S., McPherson, D., "Accurate Three-Dimensional Reconstruction of Intravascular Ultrasound Data", Circulation, 1996, pp. 567-576, vol. 93, No. 3, American Heart Association, Dallas, U.S.A.

Falk, V., Mourgues, F., Adhami, L., Jacobs, S., Thiele, H., Nitzsche, S., Mohr, F., Coste-Maniere, E., "Cardio Navigation: Planning, Simulation, and Augmented Reality in Robotic Assisted Endoscopic Bypass Grafting", The Annals of Thoracic Surgery, 2005, pp. 2040-2048, vol. 79, No. 6, Little, Brown & Co., Boston, U.S.A.

Fencil, L., Doi, K., Hoffman, K., "Accurate Analysis of Blood Vessel Sizes and Stenotic Lesions Using Stereoscopic DSA System", Investigative Radiology, 1988, pp. 33-41, vol. 23, No. 1, Lippincott, Philadelphia, U.S.A.

Fujita, H., Doi, K., Fencil, L., Chua, K., "Image Feature Analysis and Computer-Aided Diagnosis in Digital Radiography. 2. Computerized Determination of Vessel Sizes in Digital Subtraction Angiography", Medical Physics, 1987, pp. 549-556, vol. 14, No. 4, American Institute of Physics, New York, U.S.A.

Godbout, B., De Guise, J., Soulez, G., Cloutier, G., "3D Elastic Registration of Vessel Structures from IVUS data on Biplane Angiography", Academic Radiology, 2005, pp. 10-16, vol. 12, No. 1, Association of University Radiologists, Reston, U.S.A.

Guggenheim, N., Doriot, P., Dorsaz, P., Descouts, P., Rutishauser, W., "Spatial Reconstruction of Coronary Arteries from Angiographic Images", Physics in Medicine and Biology, 1991, pp. 99-110, vol. 36, No. 1, Institute of Physics, London, England.

Hoffmann, K., Sen, A., Lan, L., Chua, K., Esthappan, J., Mazzucco, M., "A System for Determination of 3D Vessel Tree Centerlines from Biplane Images", The International Journal of Cardiac Imaging, 2000, pp. 315-330, vol. 16, No. 5, Nijhoff, Boston, U.S.A.

Jiang, H., Chen, W., Wang, G., Liu, H., "Localization Error Analysis for Stereo X-ray Image Guidance with Probability Method", Medical Engineering & Physics, 2001, pp. 573-581, vol. 23, No. 8, Butterworth-Heinemann, Oxford, England.

Legget, M., Leotta, D., Bolson, E., McDonald, J., Martin, R., Li, X., Otto, C., Sheehan, F., "System for Quantitative Three-Dimensional Echocardiography of the Left Ventricle Based on a Magnetic-Field Position and Orientation Sensing System", IEEE Transactions on Biomedical Engineering, 1998, pp. 494-504, vol. 45, No. 4, Institute of Electrical and Electronics Engineers, New York, U.S.A.

Leotta, D., "An Efficient Calibration Method for Freehand 3-D Ultrasound Imaging Systems", Ultrasound in Medicine & Biology, 2004, pp. 999-1008, vol. 30, No. 7, Elsevier, New York, U.S.A.

Liu, I., Sun, Y., "Fully Automatic Reconstruction of Three-Dimensional Vascular Tree Structures from Two Orthogonal Views Using Computational Algorithms and Production Rules", Optical Engineering, 1992, pp. 2197-2207, vol. 31, No. 10, The Society of Photo-optical Instrumentation Engineers, Redondo Beach, U.S.A.

Liu, J., Goldberg, B., "2-D and 3-D Endoluminal Ultrasound: Vascular and Nonvascular Applications", Ultrasound in Medicine & Biology, 1999, pp. 159-173, vol. 25, No. 2, Elsevier, New York, U.S.A.

Meyer, C., Boes, J., Kim, B., Bland, P., LeCarpentier, G., Fowlkes, J., Roubidoux, M., Carson, P., "Semiautomatic Registration of Volumetric Ultrasound Scans", Ultrasound in Medicine & Biology, 1999, pp. 339-347, vol. 25, No. 3, Elsevier, New York, U.S.A.

Meyer, S., Wolf, P., "Registration of Three-Dimensional Cardiac Catheter Models to Single-Plane Fluoroscopic Images", IEEE Transactions on Biomedical Engineering, 1999, pp. 1471-1479, vol. 46, No. 12, Institute of Electrical and Electronics Engineers, New York, U.S.A.

Movassaghi, B., Grass, V., Viergever, M., Niessen, W., "A Quantitative Analysis of 3-D Coronary Modeling from Two or More Projection Images", IEEE Transactions on Medical Imaging, 2004, pp. 1517-1531, vol. 23, No. 12, Institute of Electrical and Electronics Engineers, New York, U.S.A.

Prause, G., DeJong, S., McKay C., Sonka, M., "Semi-Automated Segmentation and 3-D Reconstruction of Coronary Trees: Biplane Angiography and Intravascular Ultrasound Data Fusion" in *SPIE Medical imaging 1996. Physiology and function from multidimensional images* : Feb. 11-13, 1996, Newport Beach, California, 1996, pp. 82-92, vol. 2709, Ed.Hofman, E., SPIE, Bellingham, U.S.A.

Prause, G., DeJong, S., McKay, C., Sonka, M., "Accurate 3-D Reconstruction of Tortuous Coronary Vessels Using Biplane Angiography and Intravascular Ultrasound" *in SPIE Medical imaging 1997. Physiology and function from multidimensional images* : Feb. 23-25, 1997, Newport Beach, California, 1997, pp. 225-234, vol. 3033, Ed.Hofman, E., SPIE, Bellingham, U.S.A.

Rotger, D., Radeva, P., Mauri, J., Fernandez-Nofrerias, E., "Internal and External Coronary Vessel Images Registration" in *Topics in Artificial Intelligence*, 2002, pp. 408-418, Eds. Escrig Monferrer M. and Toledo Lobo, F., Springer-Verlag, Berlin, Germany.

Sheehan, H., Hodgson, J., "Intravascular Ultrasound: Advantages and Indications", International Journal of Cardiac Imaging, 1995, pp. 9-14, vol. 11, No. Suppl 1, Kluwer Academic Publishers, Boston, U.S.A.

Shekhar, R., Cothren, R., Vince, D., Cornhill, J., "Fusion of Intravascular Ultrasound and Biplane Angiography for Three-Dimensional Reconstruction of Coronary Arteries", Computers in Cardiology Conference Proceedings, 1996, pp. 5-8, vol. 23, Institute of Electrical and Electronics Engineers, Piscataway, U.S.A.

Shekhar, R., Cothren, R., Vince, D., Cornhill, J., "Spatio-Temporal Localization of Intravascular Ultrasound Data for Accurate 3D Reconstruction of Coronary Arteries", IEEE Engineering in Medicine and Biology Society Conference Proceedings, 1996, pp. 668-669, vol. 2, Institute of Electrical and Electronics Engineers, Piscataway, U.S.A.

Sherknies, D., Meunier, J., Mongrain, R., Tardif, J., "Three-Dimensional Trajectory Assessment of an IVUS Transducer from Single-Plane Cineangiograms: A Phantom Study", IEEE Transactions on Biomedical Engineering, 2005, pp. 543-548, vol. 52, No. 3, Institute of Electrical and Electronics Engineers, New York, U.S.A.

Takemura, A., Harauchi, H., Suzuki, M., Hoffmann, K., Inamura, K., Umeda, T., "An Algorithm for Mapping the Catheter Tip Position on a Fluorograph to the Three-Dimensional Position in Magnetic Resonance Angiography Volume Data", Physics in Medicine and Biology, 2003, pp. 2697-2711, vol. 48, No. 16, Institute of Physics, London, England.

Van Walsum, T., Baert, S., Niessen, W., "Guide Wire Reconstruction and Visualization in 3DRA Using Monoplane Fluoroscopic Imaging", IEEE Transactions on Medical Imaging, 2005, pp. 612-623, vol. 24, No. 5, Institute of Electrical and Electronics Engineers, New York, U.S.A.

Wahle, A., Prause, G., Von Birgelen, C., Erbel, R., Sonka, M., "Automated Calculation of the Axial Orientation of Intravascular Ultrasound Images by Fusion with Biplane Angiography" in *SPIE Medical imaging 1999. Image processing* : Feb. 22-25, 1999, San Diego, California, 1999, pp. 1094-1104, vol. 3661, Ed. Hanson, K., SPIE, Bellingham, U.S.A.

Wahle, A., Mitchell, S., Ramaswamy, S., Chandran, K., Sanka, M., "Four-Dimensional Coronary Morphology and Computational Hemodynamics" in *SPIE Medical imaging 2001 : Image processing* : Feb. 19-22, 2001, San Diego, USA, 2001, pp. 743-754, vol. 4322, Eds. Sonka, M. and Hanson, K., SPIE, Bellingham, U.S.A.

Wahle, A., Lopez, J., Pennington, E., Meeks, S., Braddy, K., Fox, J., Brennan, T., Buatti, J., Rossen, J., Sonka, M., "Effects of Vessel Geometry and Catheter Position on Dose Delivery in Intracoronary Brachytherapy", IEEE Transactions on Biomedical Engineering, 2003, pp. 1286-1295, vol. 50, No. 11, Institute of Electrical and Electronics Engineers, New York, U.S.A.

Wahle, A., Olszewski, M., Sonka, M., "Interactive Virtual Endoscopy in Coronary Arteries Based on Multimidality Fusion", IEEE Transactions on Medical Imaging, 2004, pp. 1391-1403, vol. 23, No. 11, Institute of Electrical and Electronics Engineers, New York, U.S.A.

Weichert, F., Wawro, M., Muller, H., Wilke, C., "Registration of Biplane Angiography and Intravascular Ultrasound for 3D Vessel Reconstruction", Methods of Information in Medicine, 2004, pp. 398-402, vol. 43, No. 4, F.K. Schattauer, Stuttgart, Germany.

Weichert, F., Wawro, M., Wilke, C., "A 3D Computer Graphics Approach to Brachytherapy Planning", The International Journal of Cardiovascular Imaging, 2004, pp. 173-182, vol. 20, No. 3, Kluwer Academic Publishers, Boston, U.S.A.

Japanese Patent Office, Office Action dated Aug. 7, 2011, Application No. 2008-518511, 5 pages.

Pellot, Claire et al, "An Attempt to 3D Reconstruct Vessel Morphology from X-Ray Projections and Intravascular Ultrasounds Modeling and Fusion," Computerized medical Imaging and Graphics, Pergamon Press, New York, vol. 20, No. 3, May 1, 1996, pp. 141-151.

Wahle, Andreas et al, "Geometrically Correct 3-D Reconstruction of Intravascular Ultrasound Images by Fusion with Biplane Angiography—Methods and Validation," IEEE Transactions on Medical Imaging, IEEE Service Center, Piscataway, NJ, US, vol. 18, No. 8, Aug. 1, 1999, pp. 686-699.

International Searching Authority/European Patent Office, "Supplementary European Search Report," European patent Application No. 06785661.7, mailed Nov. 2, 2010, 12 pages.

International Search Report for International Application No. PCT/US/25016 dated Jan. 18, 2007.

Written Opinion of the International Searching Authority dated Jan. 18, 2007.

* cited by examiner

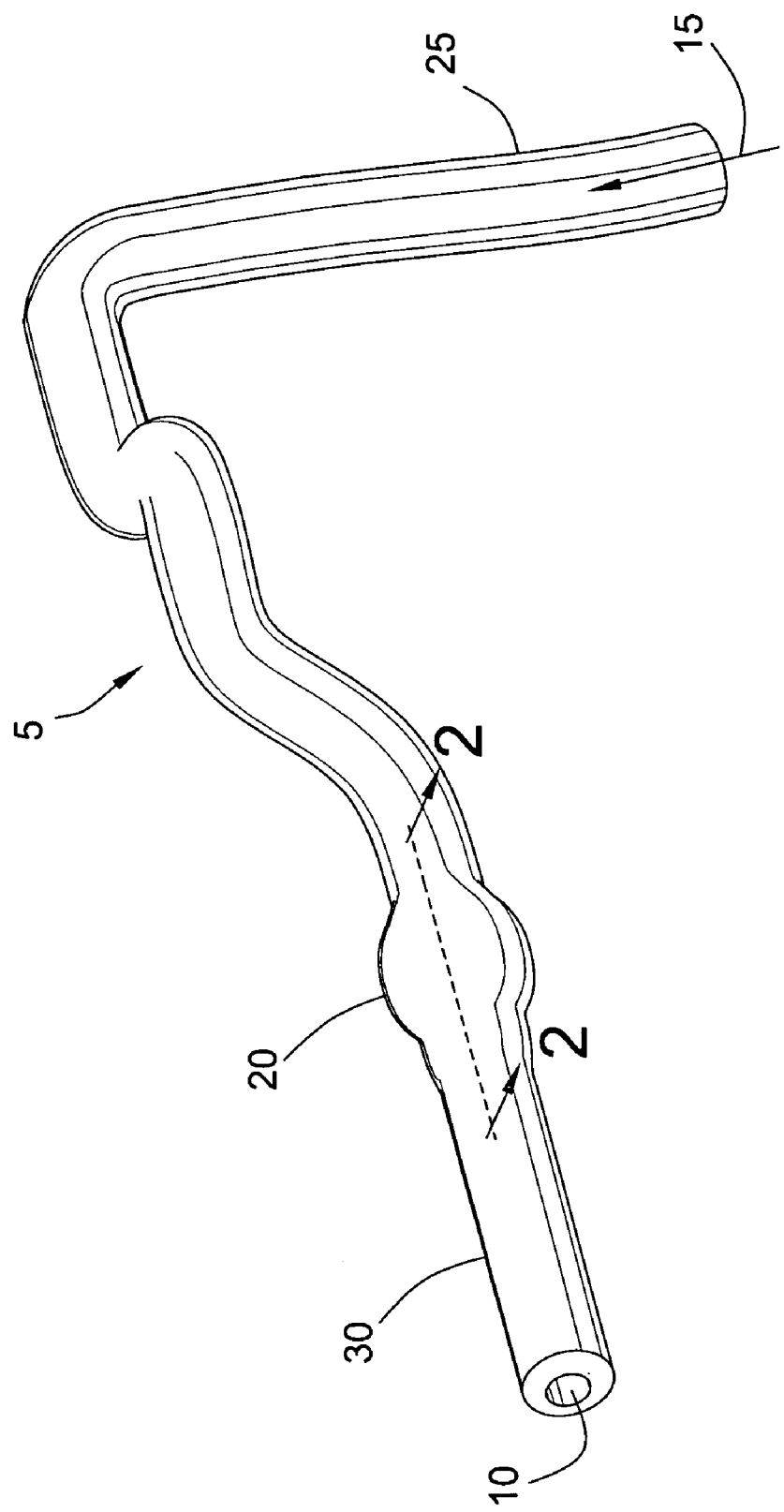

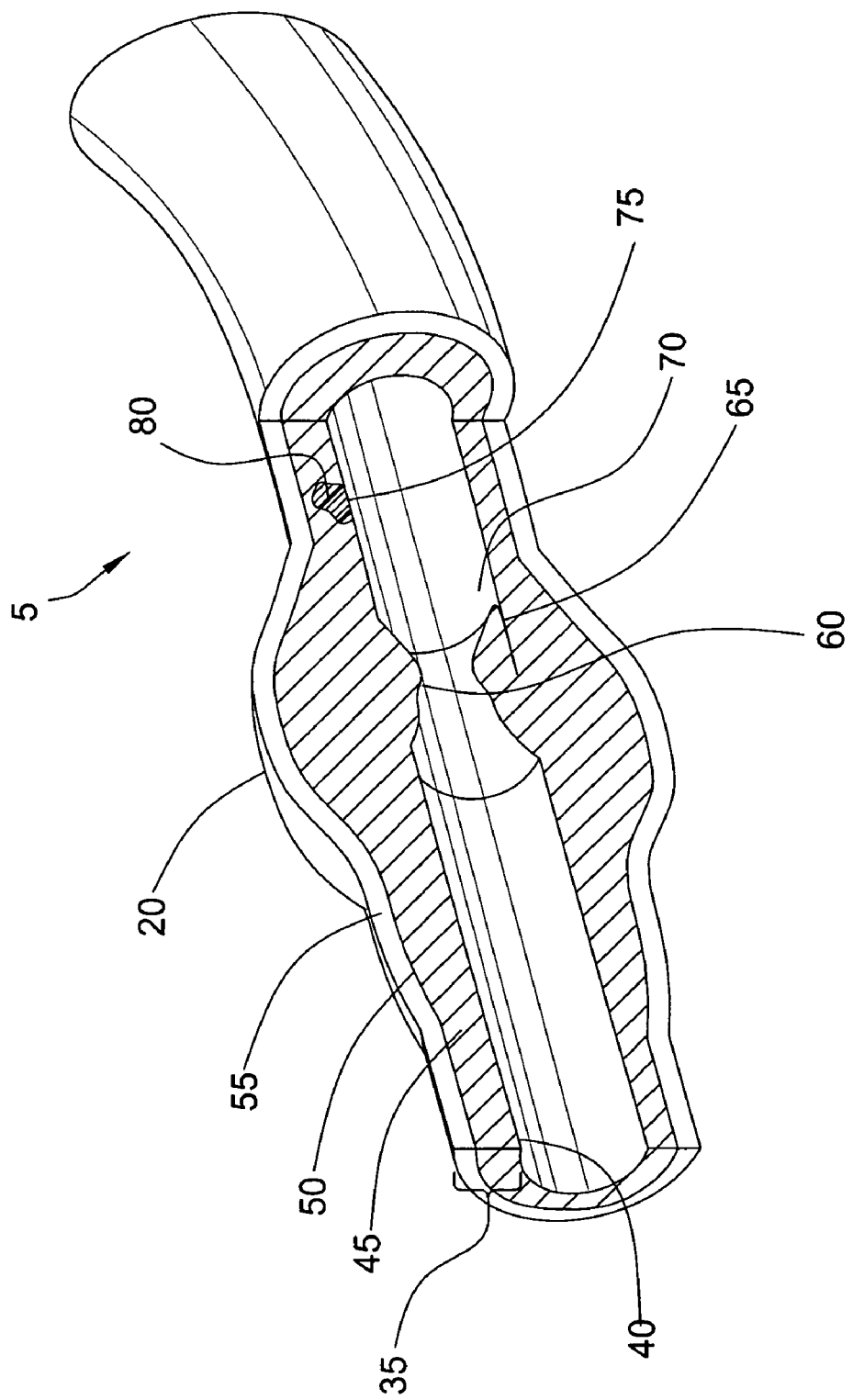

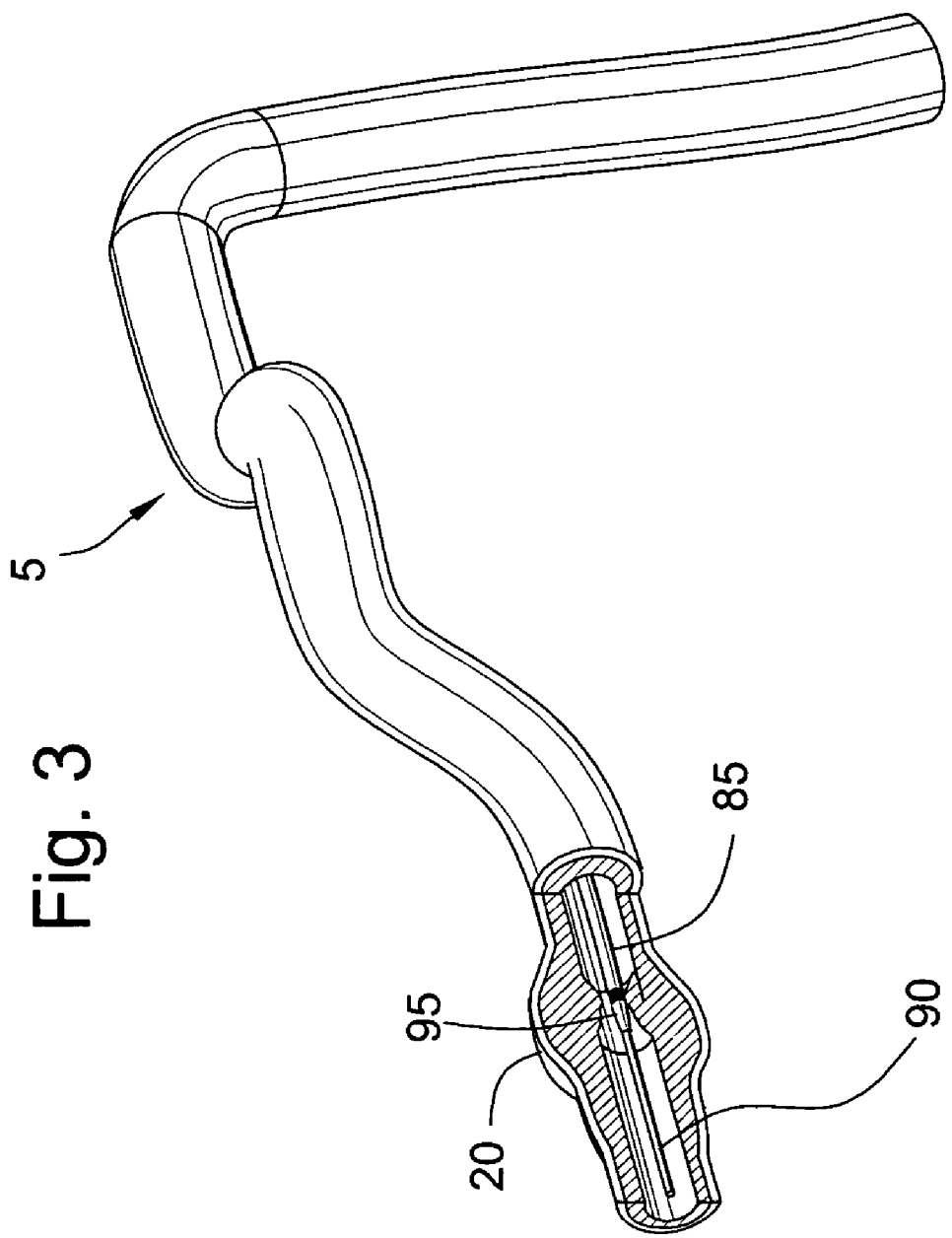

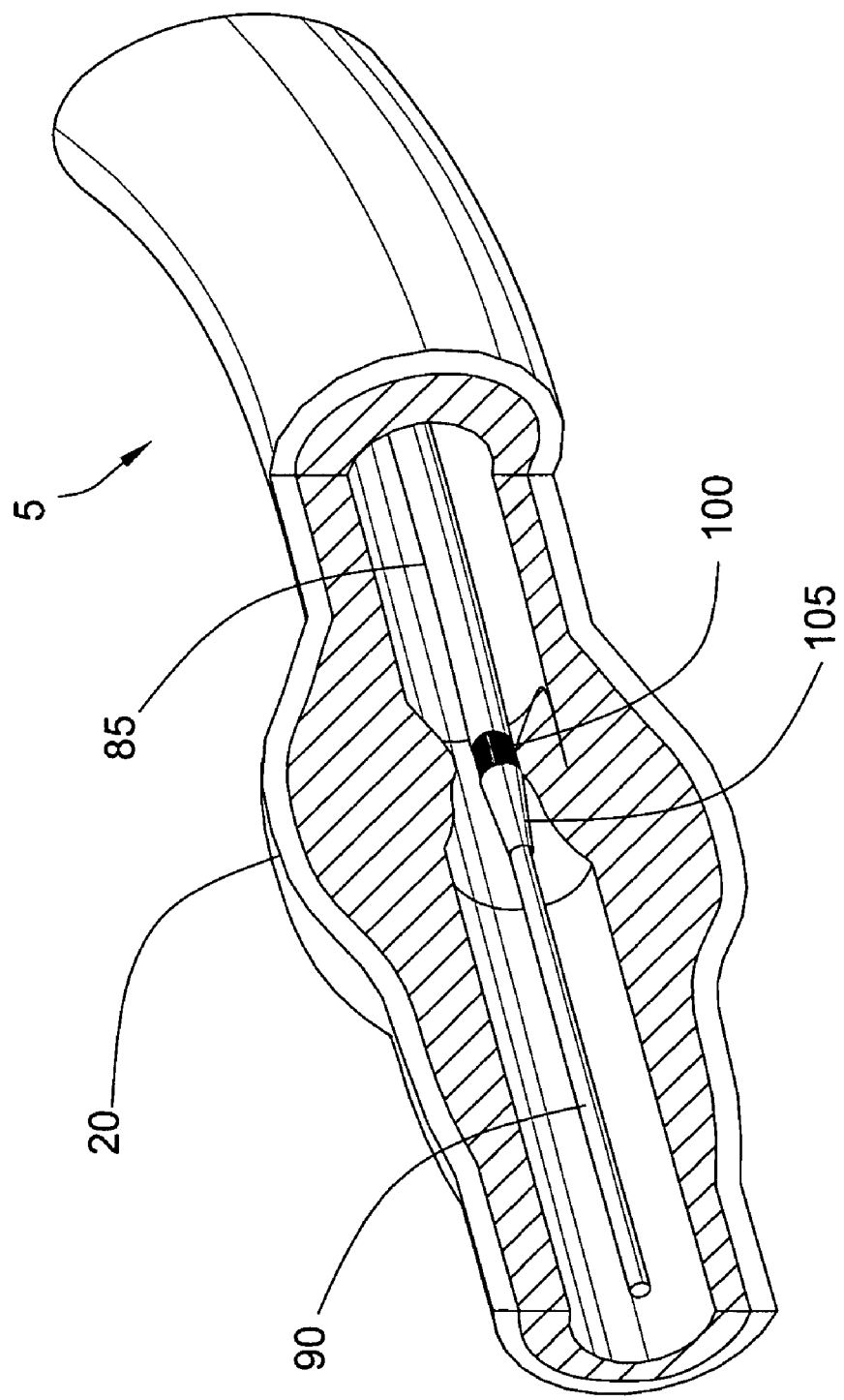

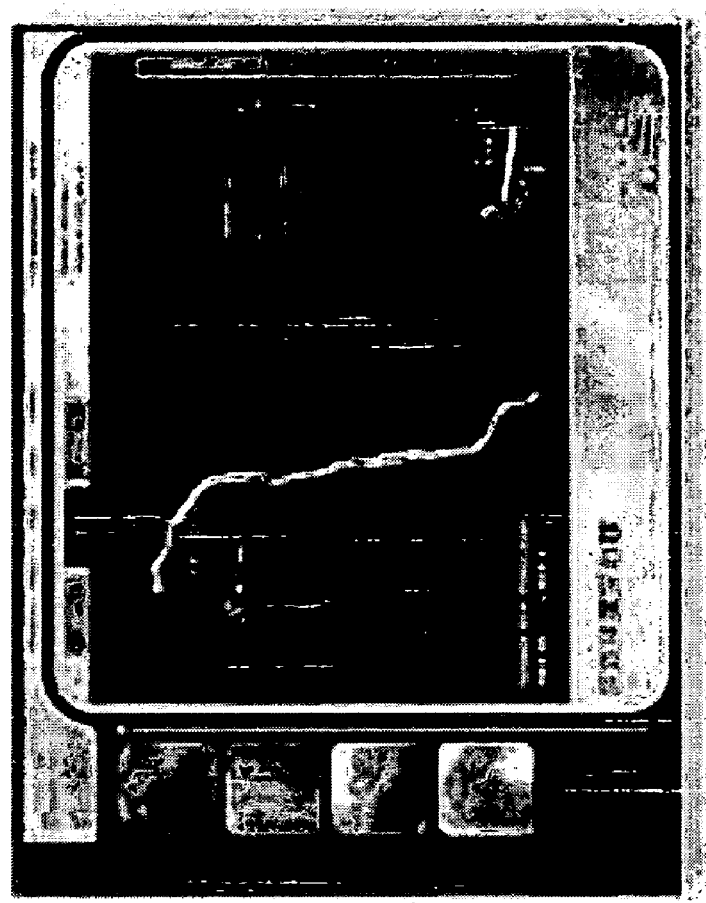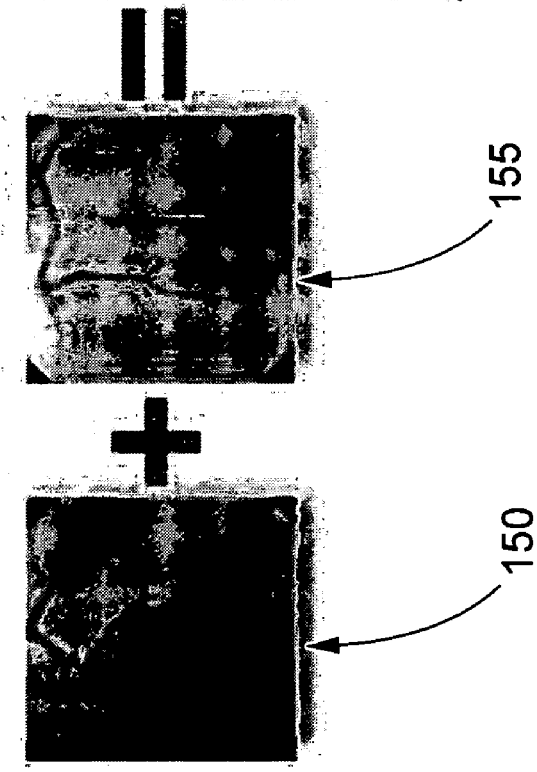
Fig. 6a PRIOR ART

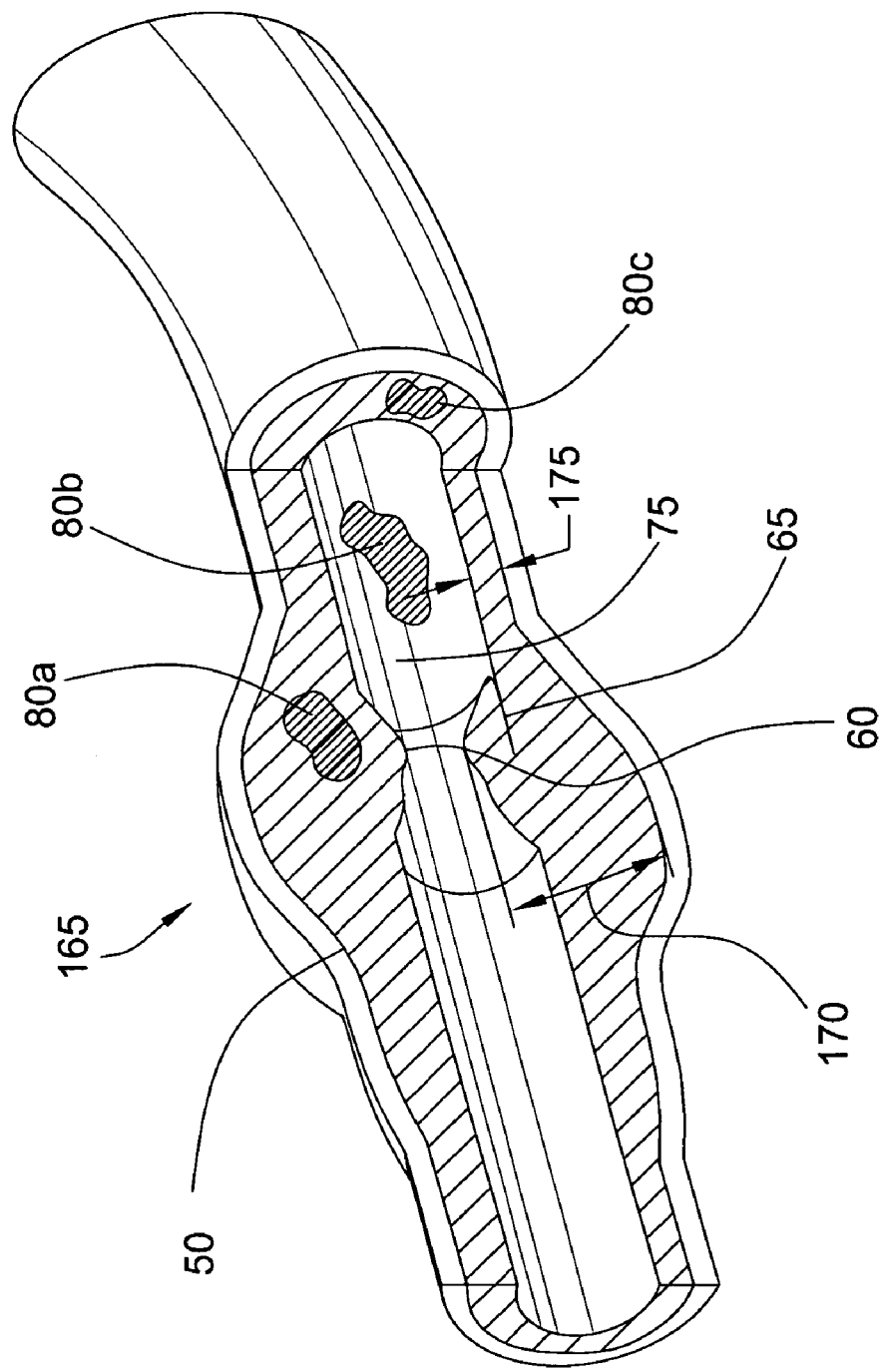

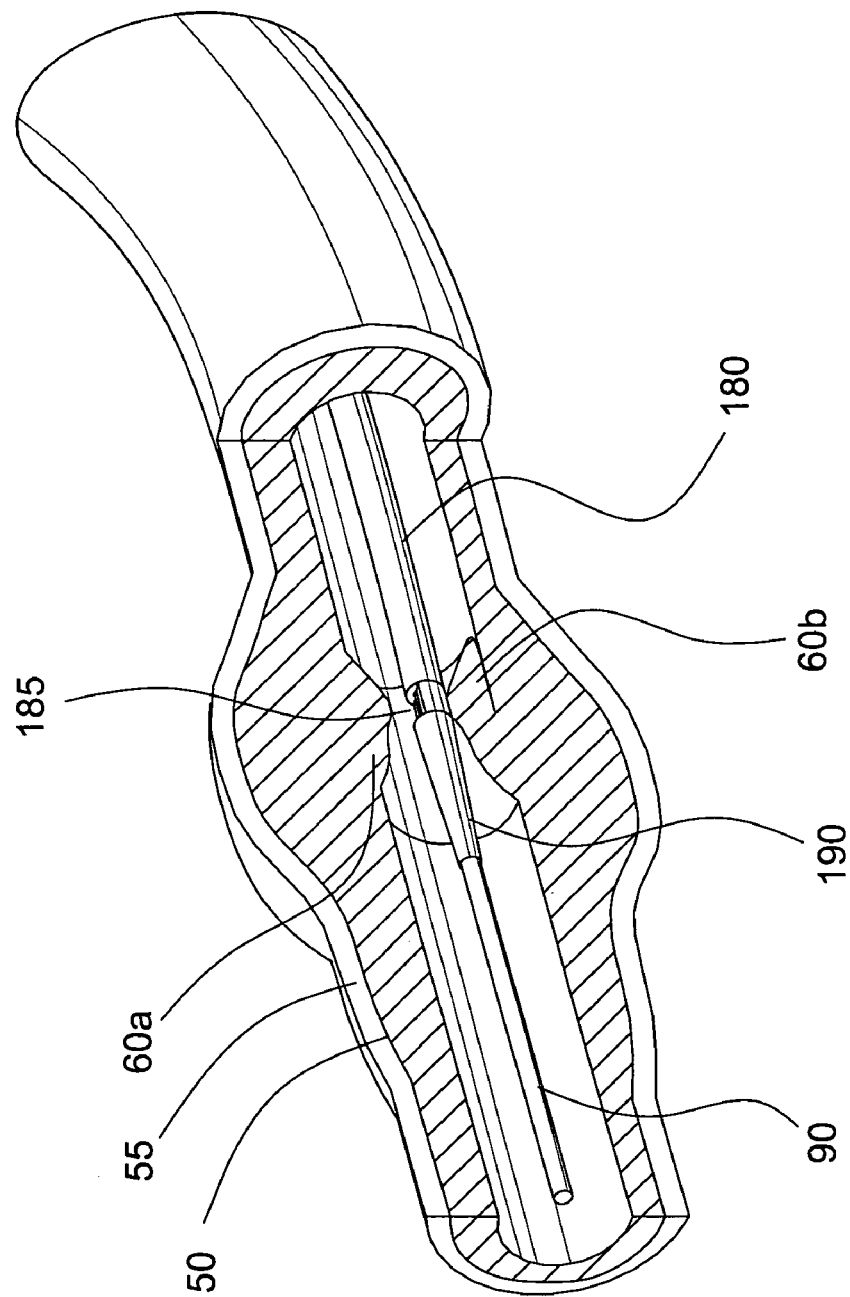

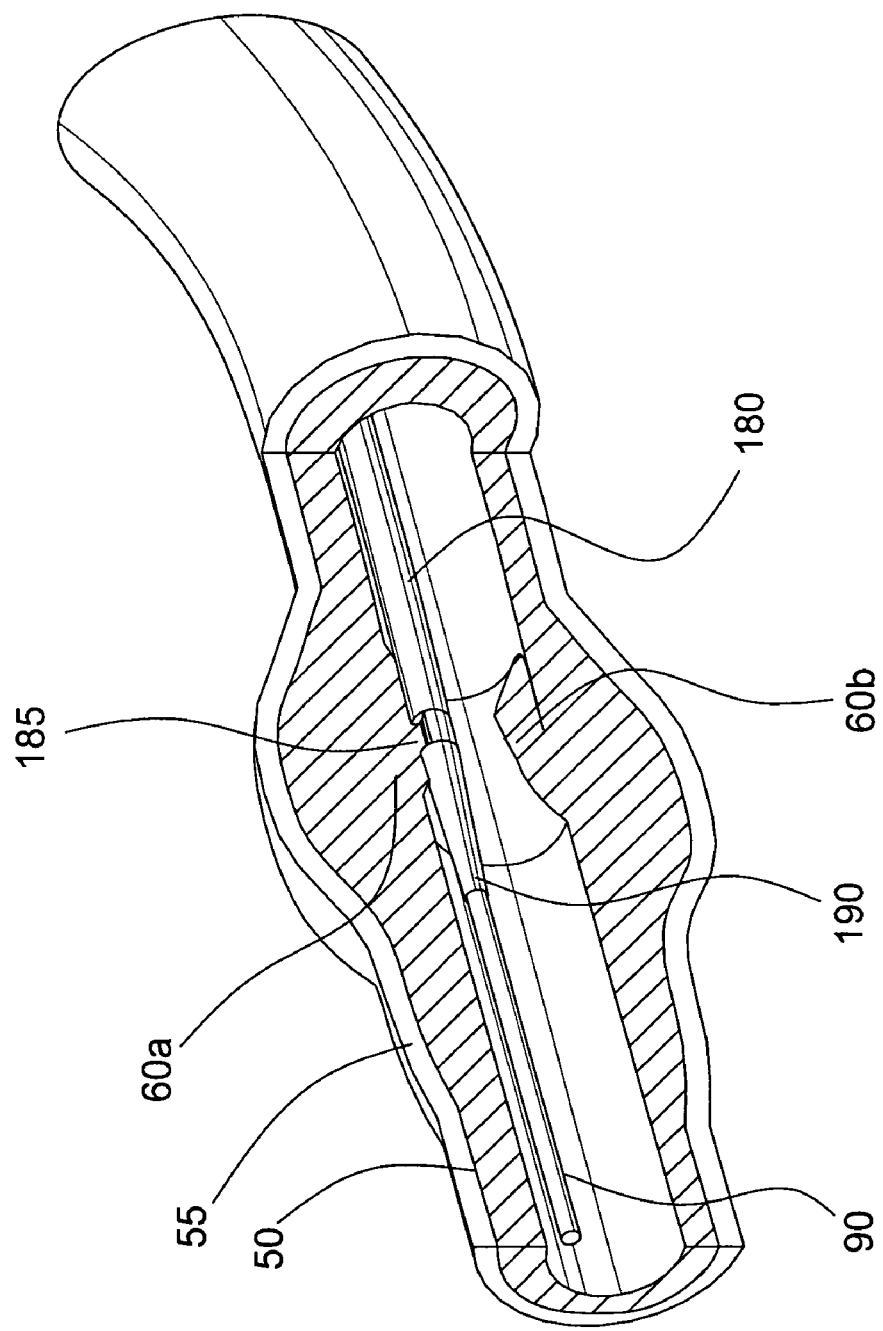

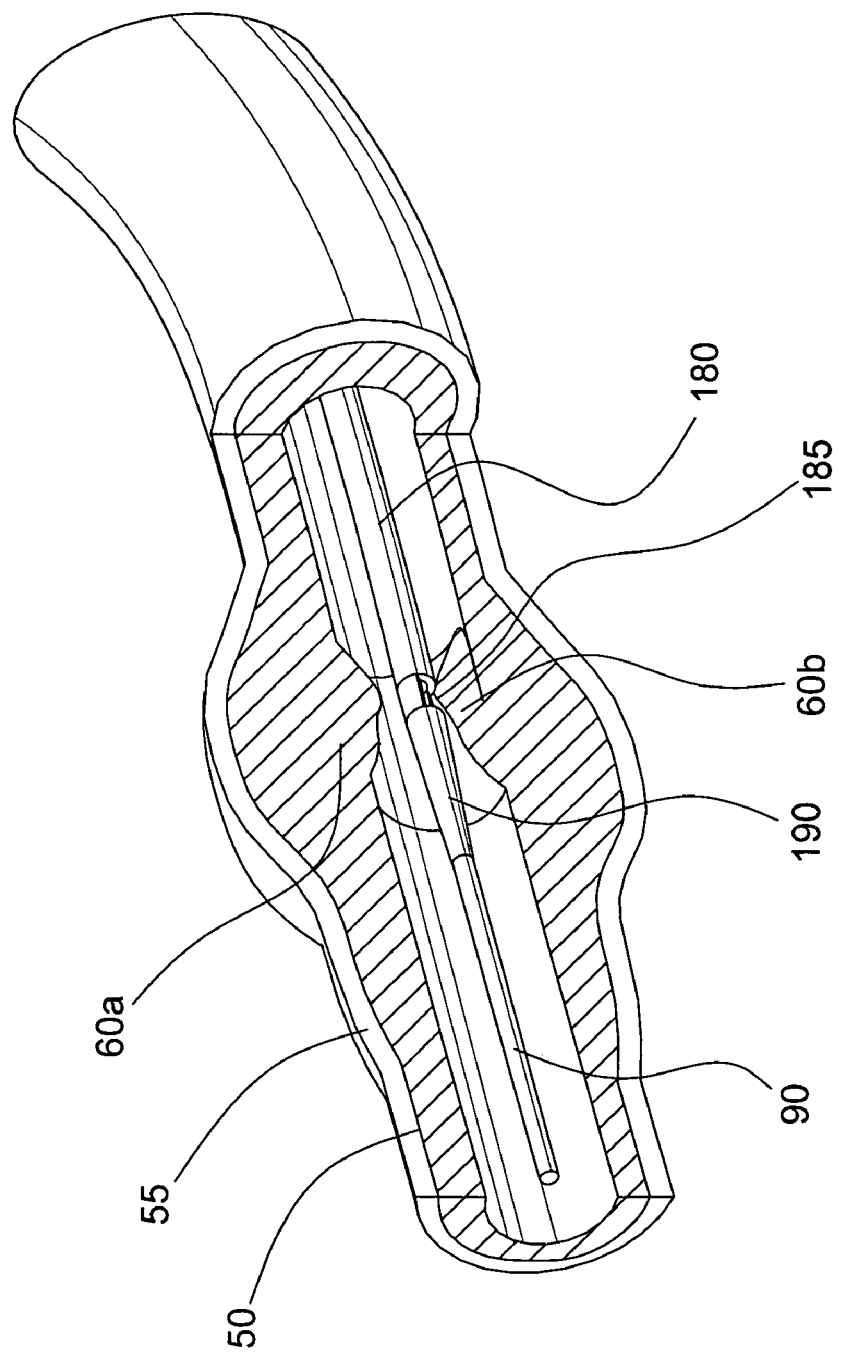

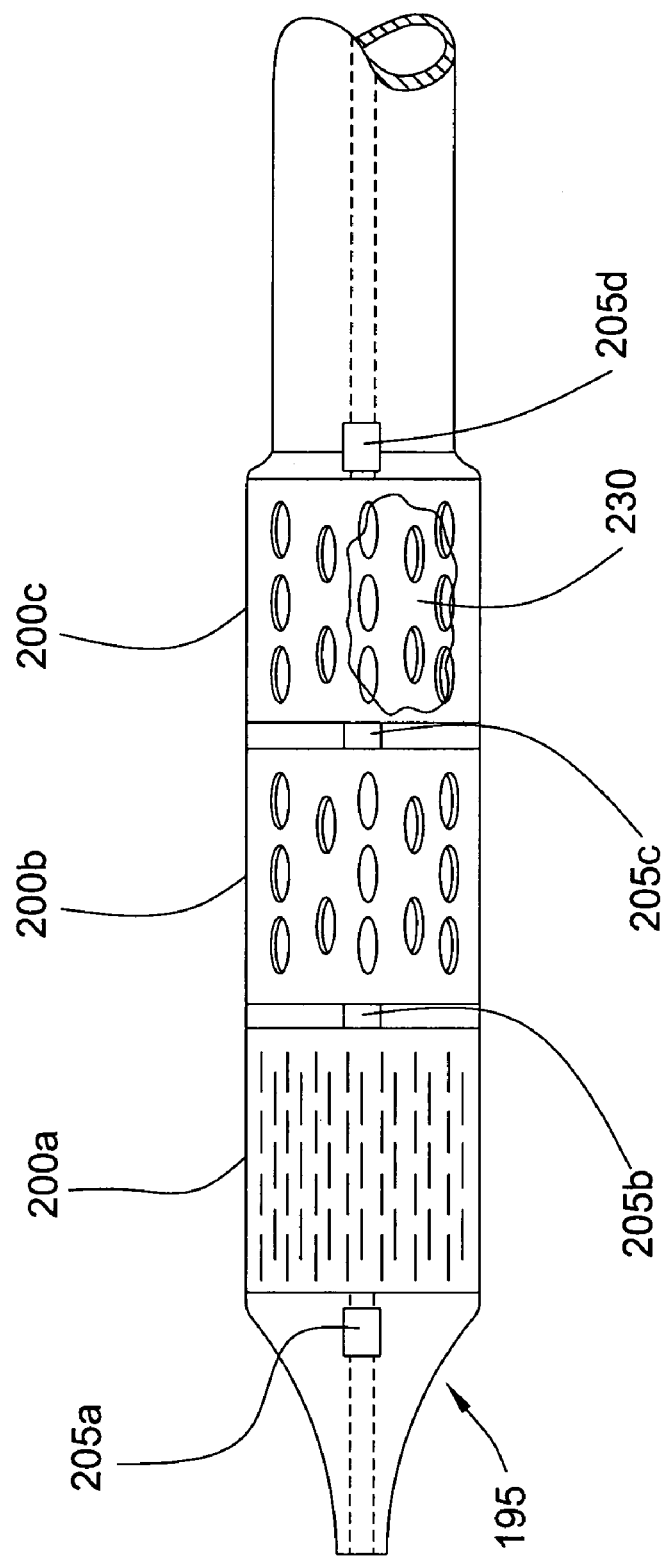

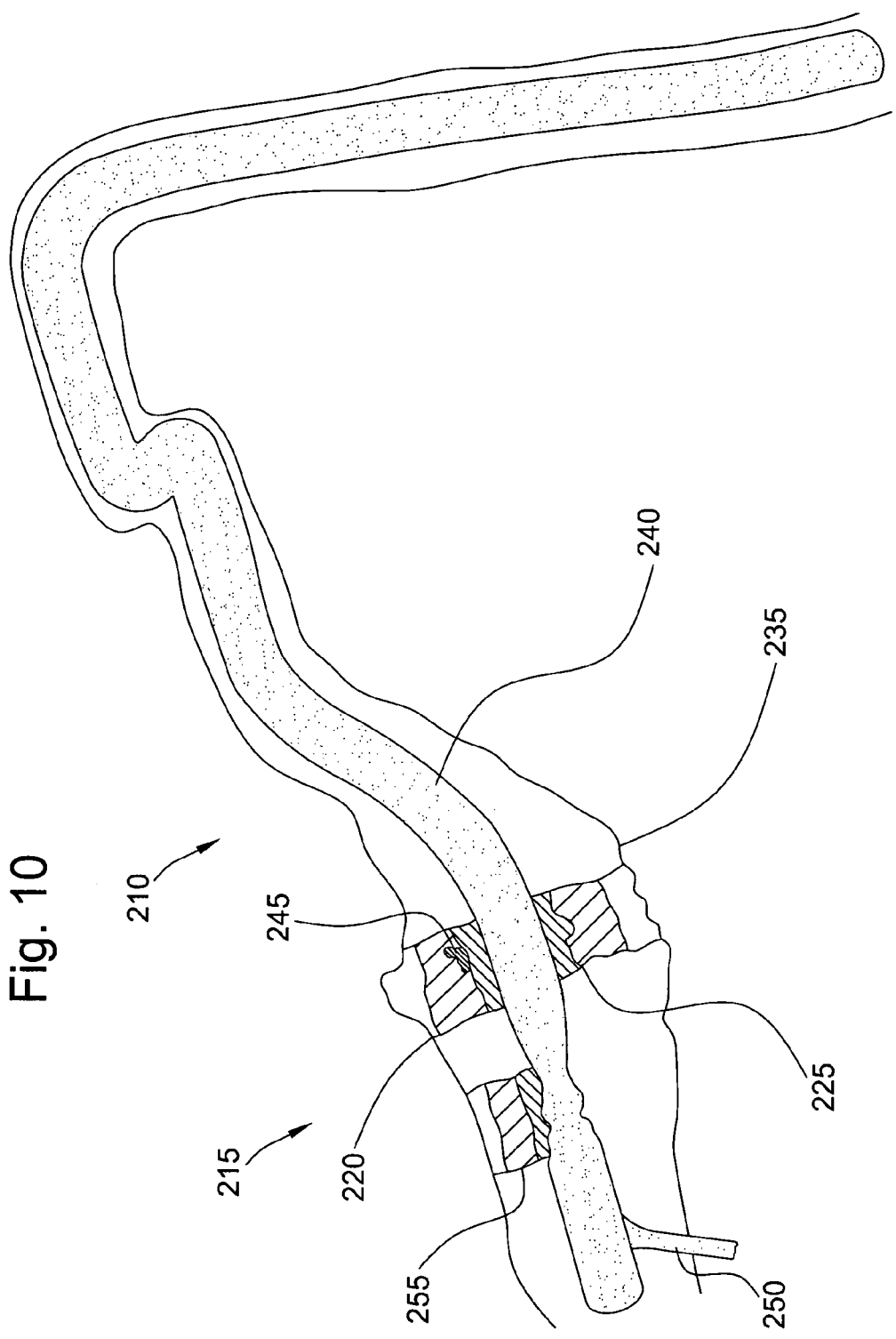

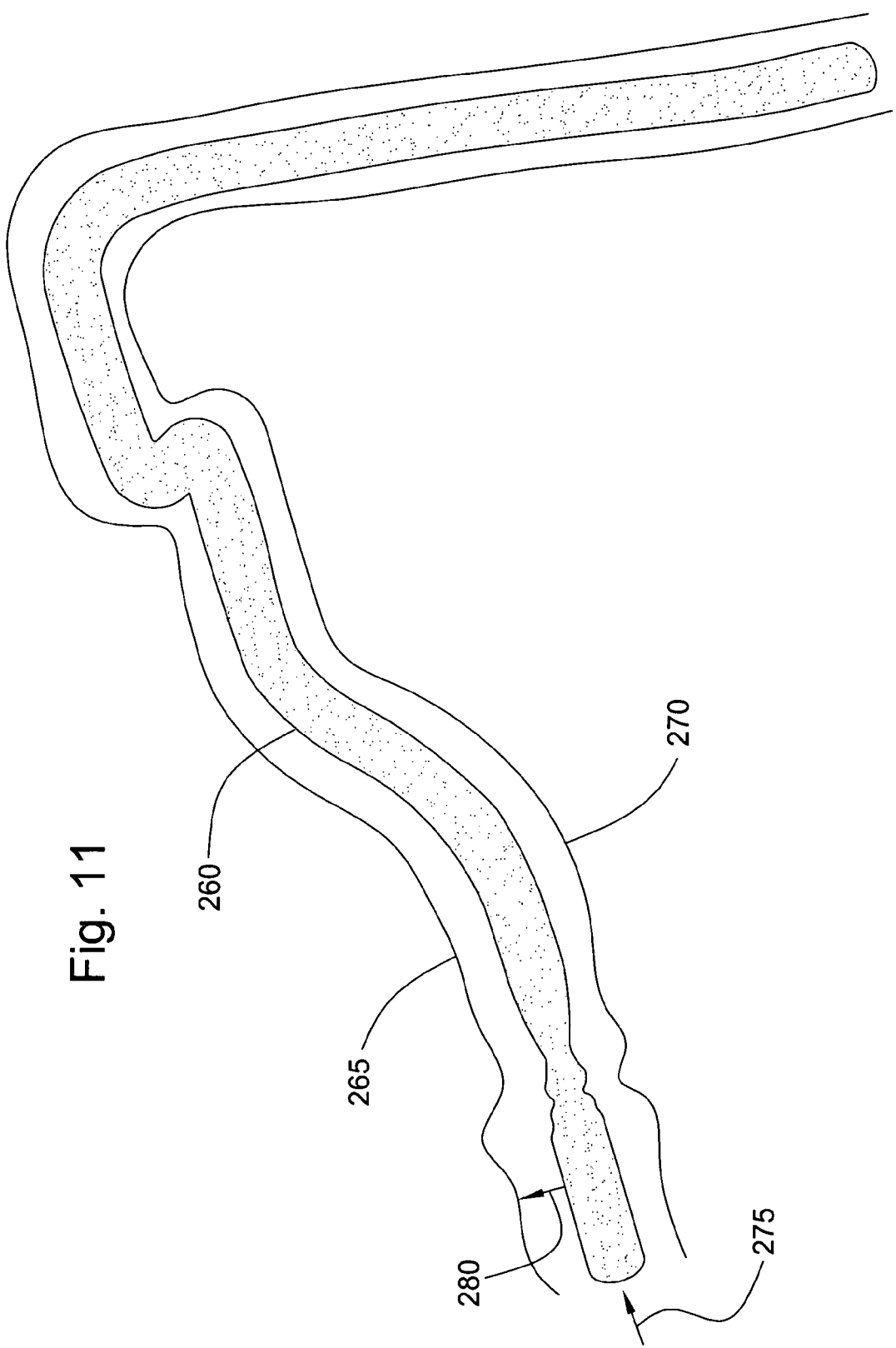

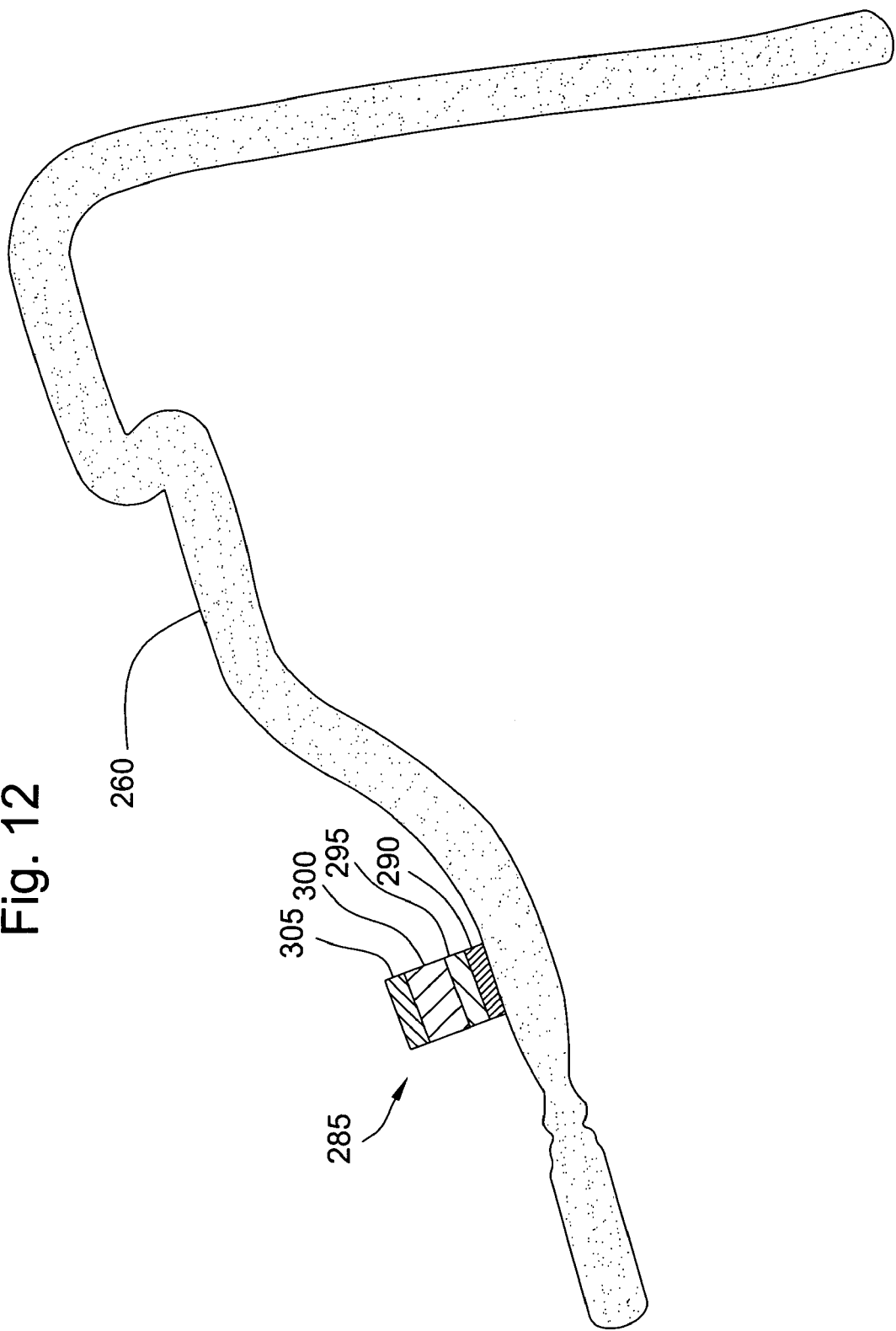

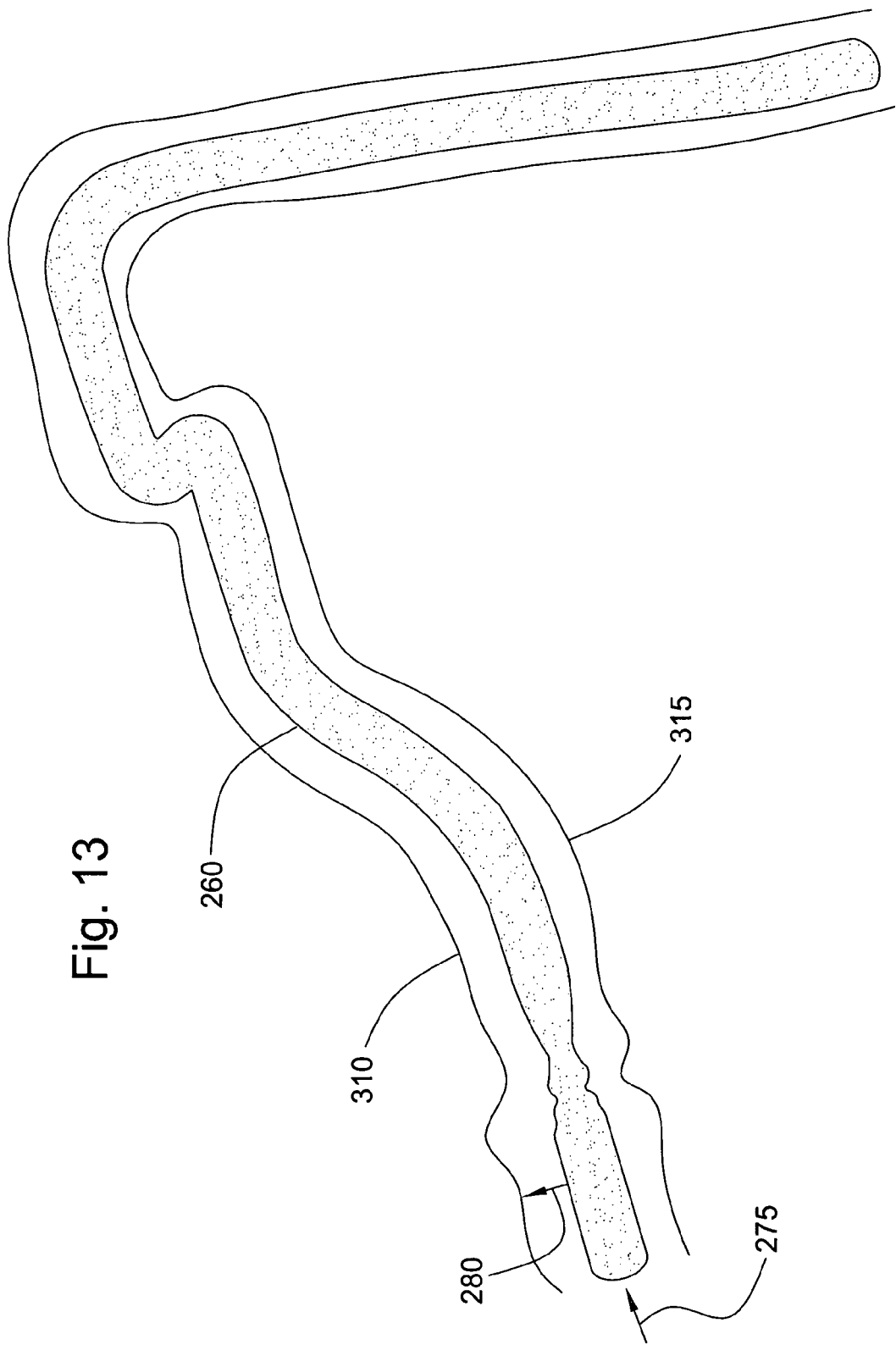

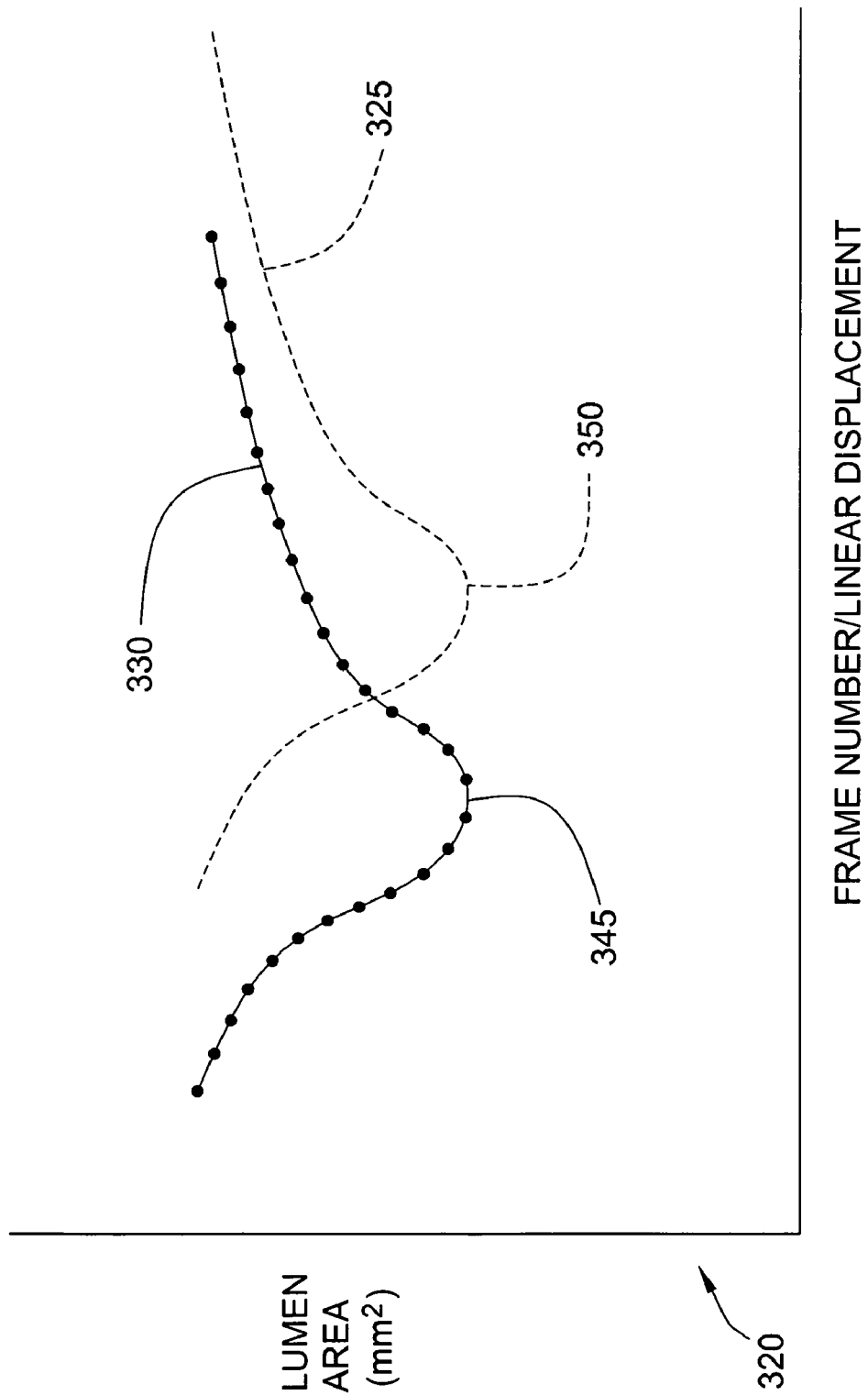

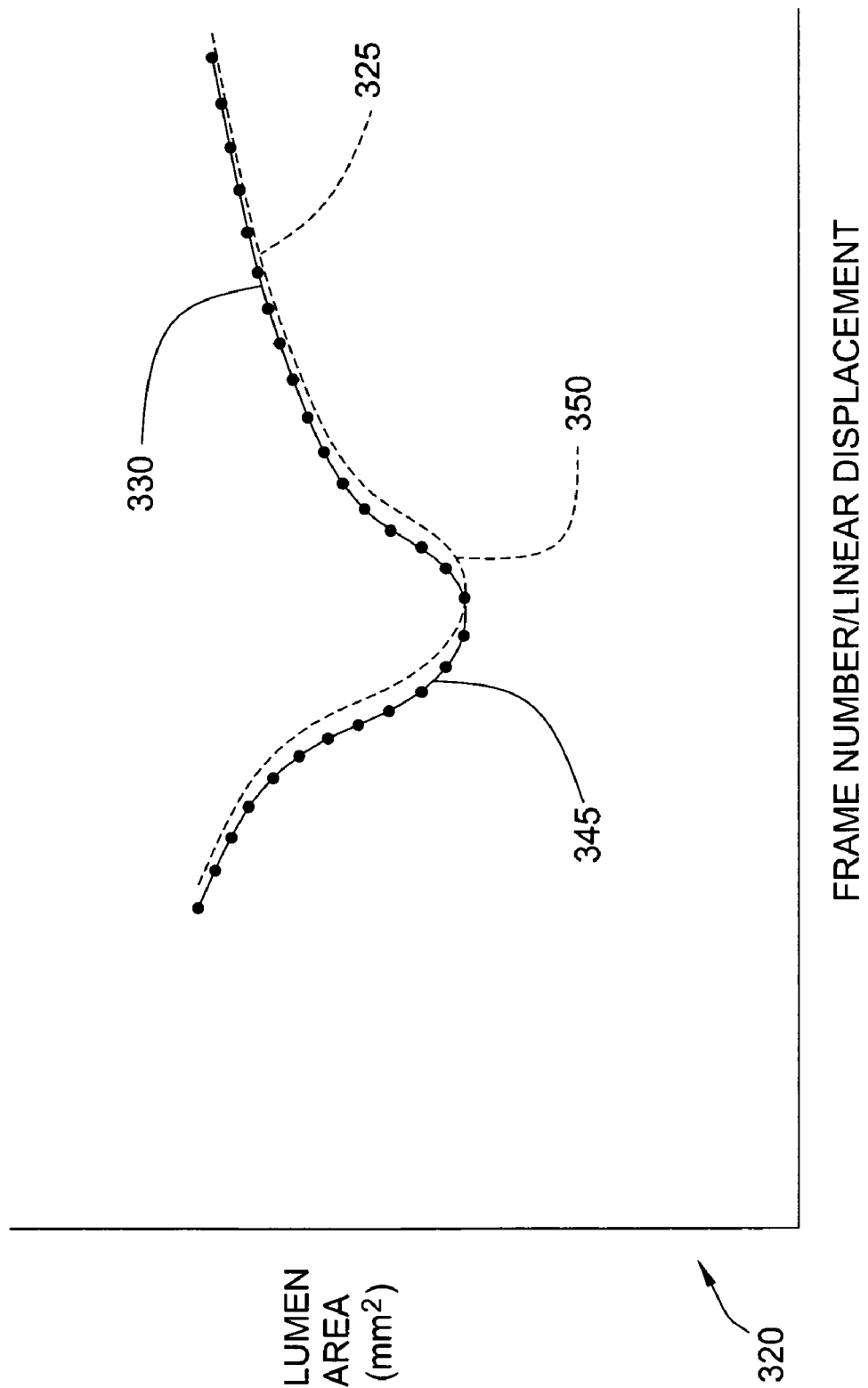

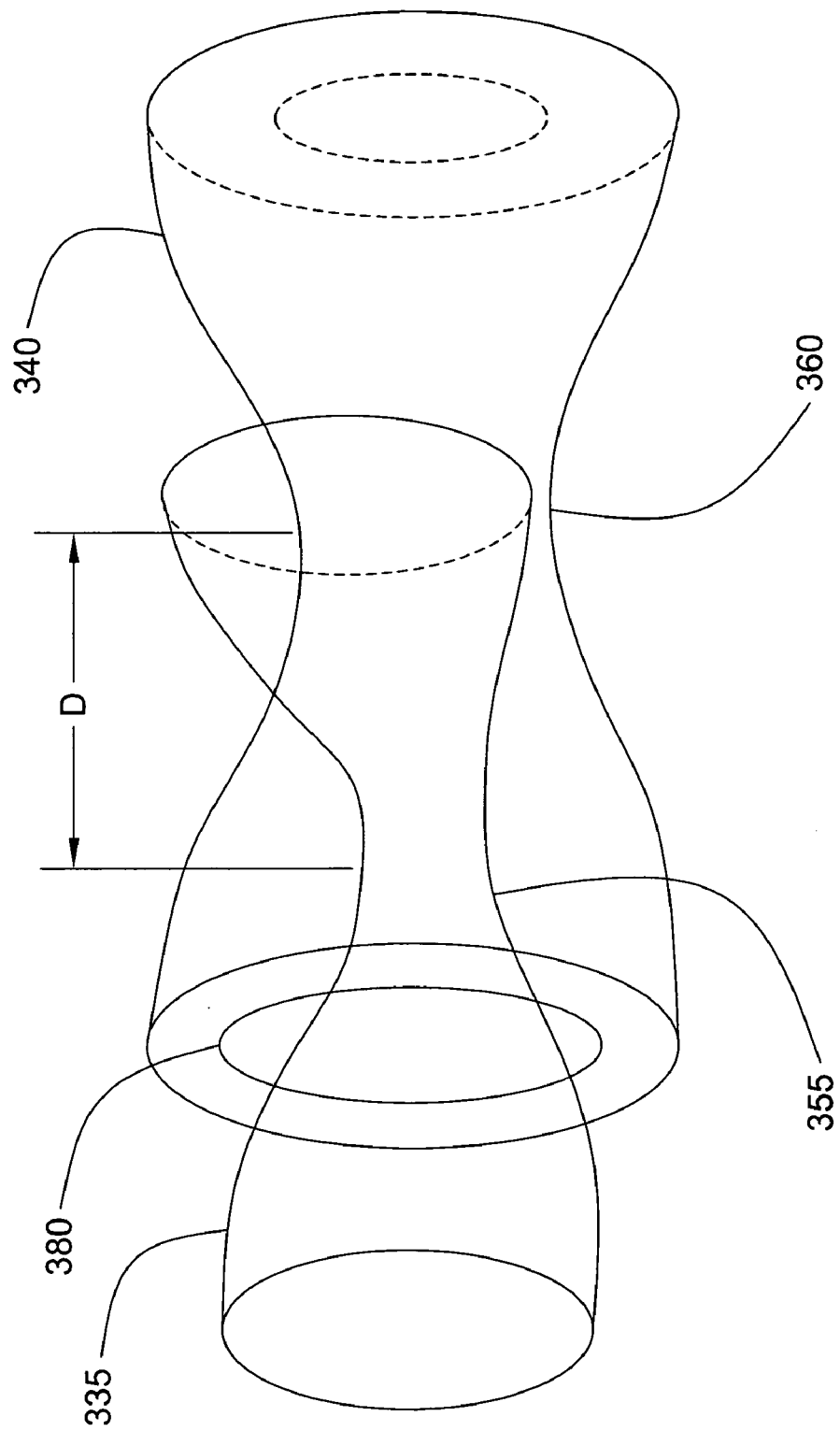

THREE DIMENSIONAL CO-REGISTRATION FOR INTRAVASCULAR DIAGNOSIS AND THERAPY

CROSS-REFERENCE TO RELATED APPLICATION

This application claims priority of Walker et al. U.S. provisional application Ser. No. 60/694,014 filed on Jun. 24, 2005, entitled "Three-Dimensional Co-Registration for Intravascular Diagnosis and Therapy", the contents of which are expressly incorporated herein by reference in their entirety including the contents and teachings of any references contained therein.

AREA OF THE INVENTION

The present invention generally relates to imaging blood vessels. More particularly, the present invention is directed to methods and systems for generating composite displays generally including at least a first graphical image rendered from a first type of data and a second graphical image rendered from a second type of data. A particular example of such composite graphical display comprises a graphically displayed three dimensional angiogram that is displayed in combination with a second graphical image created from IVUS information.

BACKGROUND OF THE INVENTION

Atherosclerosis is treated in arteries of the heart, head, neck and peripheral portions of the body using many different methods. The most popular methods, such as angioplasty, bare metal stenting, drug eluting stenting (permanently implantable and biodegradable), various types of energy delivery and rotational atherectomy, all treat an artery equally around the circumference of a target length of the arterial lumen. These devices are generally circumferentially symmetric, and cannot selectively treat one circumferential sector of the targeted length of the artery any different from another. Almost always, the targeted length of the artery identified for treatment is determined using angiography, which graphically depicts a vessel lumen, or intravascular ultrasound (IVUS), which graphically depicts the atherosclerotic plaque itself. With IVUS, the thickness of the atherosclerotic plaque can be determined along the length of the diseased area and at specific radial positions around its circumference. More often than not, the plaque is eccentric and thus varies in thickness at particular positions of a circumferential cross-sectional of the vessel. Treatment of plaque using the aforementioned circumferentially symmetric methods can sometimes cause undesired results. For example, drug eluting stents deliver drugs that inhibit neo-intimal proliferation (known as restenosis). In the section of artery where the stent is expanded, any normal (non-diseased) portion of vessel may not benefit from getting the same dosage of drug as the diseased portion.

Some methods for treating atherosclerosis, such as directional athrectomy, needle aided drug injection or certain types of brachytherapy (radiation), can actually vary the treatment along different circumferential sectors of the artery. The catheters used for these treatment methods are typically circumferentially asymmetric and have at least a portion that is torquable (rotatable), and thus able to be steered into a desired circumferential orientation. However, effective use of the asymmetric treatments is difficult because of certain characteristics of current imaging methods. For example, because angiography only shows an image of the lumen of the blood vessel, it is impossible to identify exactly where, in a particular circumferential cross-section, the atherosclerotic plaque is located and the plaque's thickness. IVUS does make it possible to view the circumferential location and thickness of atherosclerotic plaque in a length of a vessel, but unless the ultrasonic transducer is attached to the actual treatment device, it is difficult to use the IVUS image to direct the treatment catheter with precision. This is especially difficult in coronary arteries, where heart motion adds error. Attempts to include transducers on the treatment catheter have been moderately successful (U.S. Pat. No. 6,375,615 to Flaherty) but the additional components make it more difficult to build a small catheter, which is flexible and can track easily in the artery. Some other catheters have been developed (U.S. Pat. Nos. 4,821,731 and 5,592,939, both to Martinelli) which can combine IVUS imaging with tip positioning technology. This enables displaying a three dimensional graphical representation of the plaque, including any tortuosity inherent in the artery. However, additional capital equipment is required in the procedure room to perform this type of imaging and adds cost to performing the procedure.

Most of the methods described above are predominantly used to improve blood flow in stenosed areas of the artery, thus allowing for better delivery of blood to downstream tissue. Recently, more attention has been paid to vulnerable plaque—plaque that is prone to rupture, even though it may not actually be a stenotic lesion that limits flow prior to rupture. This is especially critical in coronary arteries, where a lesion rupture, combined with thrombosis, can cause a serious or even fatal myocardial infarction (heart attack). The lesion rupture can actually cause material, such as tissue factor, to dump out of the plaque, into the bloodstream, forcing the blood into a hypercoagulable state. Currently, angiography is of limited value in identifying vulnerable plaque, because this plaque is often non-stenotic, and looks similar to the normal vessel on an angiogram. New tissue characterization methods associated with IVUS (U.S. Pat. No. 6,200,268 to Vince and U.S. Pat. Nos. 6,381,350,7,074,188, and 7,359,554 to Klingensmith, as well as U.S. patent application Ser. No. 10/647,977, show promise for identifying vulnerable plaque, and a patient having a significant amount of vulnerable plaque. There are currently no standard methods to treat patients having vulnerable plaque once such patients are identified.

SUMMARY OF THE INVENTION

Creating, in a coordinated manner, graphical images of a body including vascular features from a combination of image data sources, in accordance with the present invention, comprises initially creating an angiographic image of a vessel segment. The angiographic image is, for example, either a two or three dimensional image representation. Next, a vessel image data set is acquired that is distinct from the angiographic image data. The vessel image data set comprises information acquired at a series of positions along the vessel segment. An example of such vessel image data is a set of intravascular ultrasound frames corresponding to circumferential cross-section slices taken at various positions along the vessel segment. The angiographic image and the vessel image data set are correlated by comparing a characteristic rendered independently from both the angiographic image and the vessel image data at positions along the vessel segment.

The aforementioned steps are performed in a variety of imaging environments/modalities to render a broad variety of graphical displays of three-dimensional image data for carrying out a variety of diagnostic and treatment regimens including, for example, balloon angioplasty and atherectomy procedures.

BRIEF DESCRIPTION OF THE DRAWINGS

While the claims set forth the features of the present invention with particularity, the invention, together with its objects and advantages, may be best understood from the following detailed description taken in conjunction with the accompanying drawing of which:

FIG. 1 is a graphical illustration of a three dimensional length of artery, including a highly diseased segment;

FIG. 2 is a graphical illustration of a portion of the artery depicted in FIG. 1 with a longitudinal section removed along lines 2 to illustratively depict different elements of atherosclerotic plaque;

FIG. 3 is a graphical illustration of the artery from FIGS. 1 and 2 wherein an imaging catheter has been inserted in the artery;

FIG. 4 is detailed view of a section of the artery depicted in FIG. 3 including an imaging catheter in the artery;

FIG. 6a is a set of graphical images depicting a three-dimensional reconstruction method using two two-dimensional angiographic images;

FIG. 7 illustratively depicts a vessel reconstruction graphical image based on image creation techniques embodied in a system and method incorporating the present invention;

FIGS. 8a, 8b and 8c illustratively depict the use of a directional atherectomy catheter according to guidance provided from the vessel reconstruction;

FIG. 9 illustratively depicts a series of custom, single link stents which have been crimped onto a dilatation balloon for placement in a diseased blood vessel;

FIG. 10 illustratively depicts a graphical display image including an overlay of the reconstruction over a live two-dimensional angiographic image;

FIG. 11 illustratively depicts a first graphic display in relation with a graphical representation of a three-dimensional or two-dimensional image;

FIG. 12 illustratively depicts a second graphic display in relation with a graphical representation of a three-dimensional or two dimensional image;

FIG. 13 illustratively depicts a third graphic display in relation with a graphical representation of a three-dimensional or two-dimensional image;

FIG. 14 illustratively depicts a graph including two separate sequences of values corresponding to lumen area, in relation to image frame number and linear displacement along an imaged vessel, prior to axial registration adjustment;

FIG. 15 illustratively depicts a graph including two separate sequences of values corresponding to lumen area, in relation to image frame number and linear displacement along an imaged vessel, after axial registration adjustment;

FIG. 16 illustratively depicts a graphical display of angiography and vessel (e.g., IVUS) images on a single graphical display prior to axial registration adjustment;

DETAILED DESCRIPTION OF THE DRAWINGS

Figure 5A:
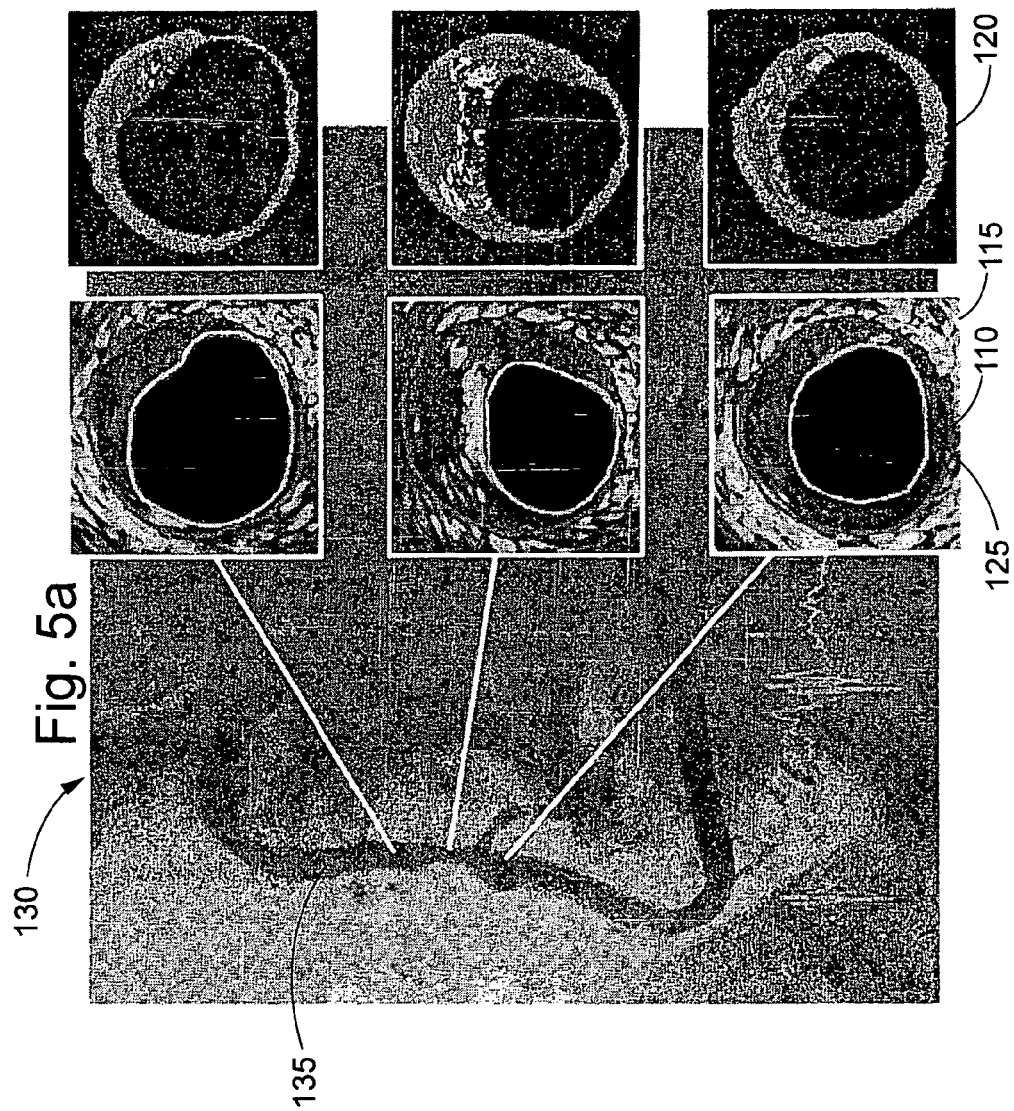
FIGS. 5a and 5b show graphical display interfaces rendered by a tissue characterization system for use with intravascular ultrasound (IVUS)

In FIG. 1, a diseased artery 5 with a lumen 10 is shown. Blood flows through the artery 5 in a direction indicated by arrow 15 from proximal end 25 to distal end 30. A stenotic area 20 is seen in the artery 5. FIG. 2 shows a sectioned portion of the stenotic area 20 of the artery 5. An artery wall 35 consists of three layers, an intima 40, a media 45 and an adventitia 55. An external elastic lamina (EEL) 50 is the division between the media 45 and the adventitia 55. A stenosis 60 is located in the artery 5 and limits blood flow through the artery. A flap 65 is shown at a high stress area 70 of the artery 5. Proximal to the stenosis 60 is an area of vulnerability 75, including a necrotic core 80. A rupture commonly occurs in an area such as the area of vulnerability 75.

FIG. 3 illustratively depicts an imaging catheter 85 having a distal end 95 that is inserted into the stenotic area 20 of the artery 5. The imaging catheter 85 is inserted over a guidewire 90, which allows the imaging catheter 85 to be steered to the desired location in the artery 5. As depicted in FIG. 4, the imaging catheter 85 includes an imaging element 100 for imaging the diseased portions and normal portions of the artery 5. The imaging element 100 is, for example, a rotating ultrasound transducer, an array of ultrasound transducer elements such as phased array/cMUT, an optical coherence tomography element, infrared, near infrared, Raman spectroscopy, magnetic resonance (MRI), angioscopy or other type of imaging technology. Distal to the imaging element 100 is a tapered tip 105 which allows the imaging catheter 85 to easily track over the guidewire 90, especially in challenging tortuous, stenotic or occluded vessels. The imaging catheter 85 can be pulled back or inserted over a desired length of the vessel, obtaining imaging information along this desired length, and thereafter creating a volumetric model of the vessel wall, including the diseased and normal portions, from a set of circumferential cross-section images obtained from the imaging information. Some technologies, such as IVUS, allow for the imaging of flowing blood and thrombus.

Figure 5B:
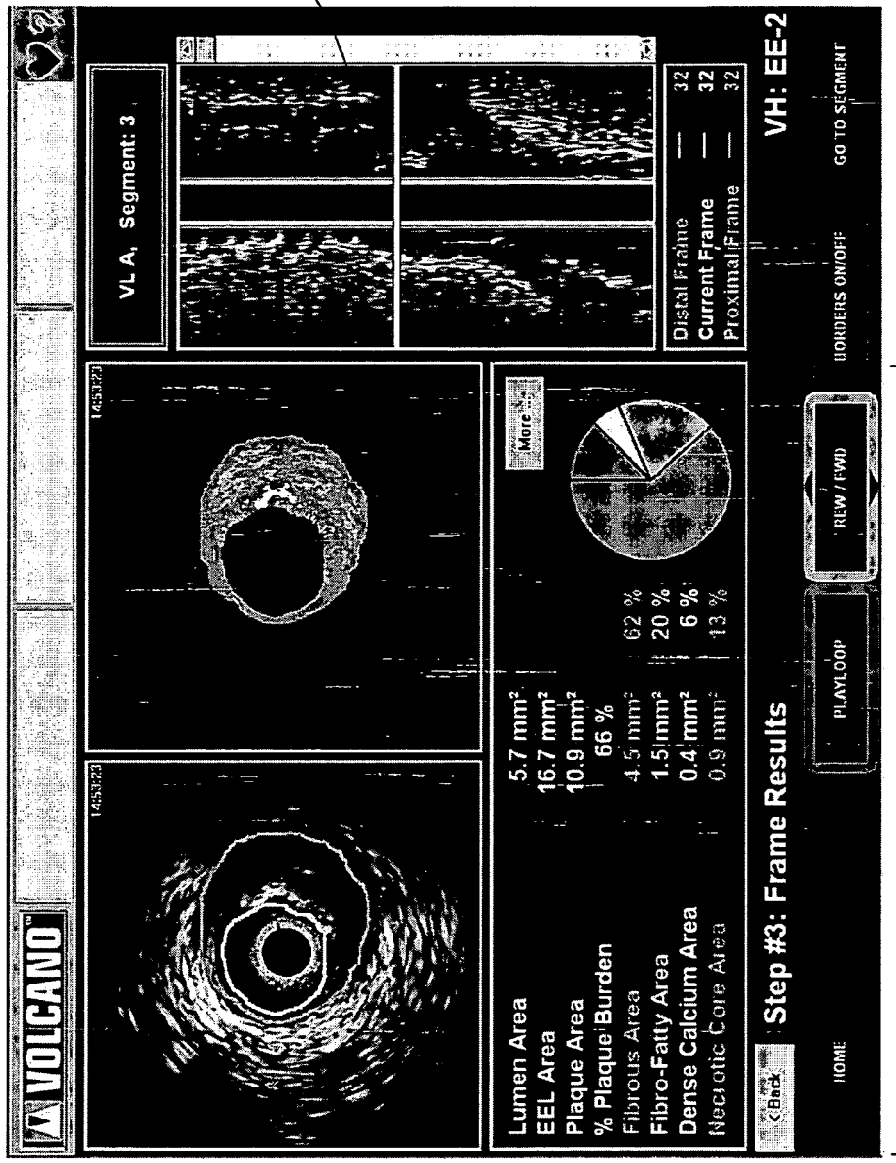

FIGS. 5a and 5b illustratively depict, by way of example, features of a vascular tissue characterization system marketed by Volcano Corporation. As graphically depicted in angiogram 130, a two dimensional image of an artery lumen 135 on its own does not provide visual information about atherosclerotic plaque that is attached to walls of an artery containing the lumen 135. Instead the angiogram 130 only depicts information about a diameter/size of the lumen 135 through which blood flows. A Gray scale IVUS cross-sectional image 115 demonstrates a cross-sectional view of the lumen 135 and atherosclerotic plaque that surrounds the lumen. Known automatic border detection algorithms executed by an IVUS image data processing system facilitate identifying a luminal boundary 125 and an EEL 110. Plaque components are identified from information derived from IVUS radiofrequency backscatter and are color coded. The various characterized and graphically depicted plaque components potentially consist, by way of example, fibrous, fibro-lipidic (fibro fatty), necrotic core, calcified (dense calcium), blood, fresh thrombus, and mature thrombus. The RF backscatter can also give information to identify and color code stent materials such as metallic or polymeric stents. The distribution of components in a cross-section or in the entire volume of the vessel analyzed is displayed by way of example through various graphics depicted in a bracketed portion 145 of an exemplary graphical display depicted in FIG. 5*b*. In addition to the cross-sectional display images rendered in portion 145, a longitudinal display region 140 is also included in the illustrative graphical display in FIG. 5*b* that depicts information obtained from portions of a set of circumferential cross-sectional slides.

FIG. 6*a* illustratively depicts the general concept behind a prior art three-dimensional reconstruction analysis system. A first two-dimensional angiographic image 150 taken in a first view plane and a second two-dimensional angiographic image 155, taken in a second view plane differing from the first view plane are combined and analyzed to create a graphical representation of a three-dimensional image depicted on a graphical display 160. The image displayed on the graphical display 160 provides a much more realistic graphical representation of a lumen of an actual artery (or other blood vessel) than the typical two-dimensional angiography images.

In accordance with an aspect of an imaging system embodying the present invention, IVUS images are co-registered with the three-dimensional image depicted on the graphical display 160. Fiduciary points are selected when the imaging catheter is at one or more locations, and by combining this information with pullback speed information, a location vs. time (or circumferential cross-sectional image slice) path is determined for the imaging probe mounted upon the catheter. Co-registering cross-sectional IVUS with three-dimensional images of the type depicted in FIG. 6*a* allows for a three-dimensional volumetric map of either gray scale images or colorized tissue characterization (tissue composition) images.

Figure 6B:
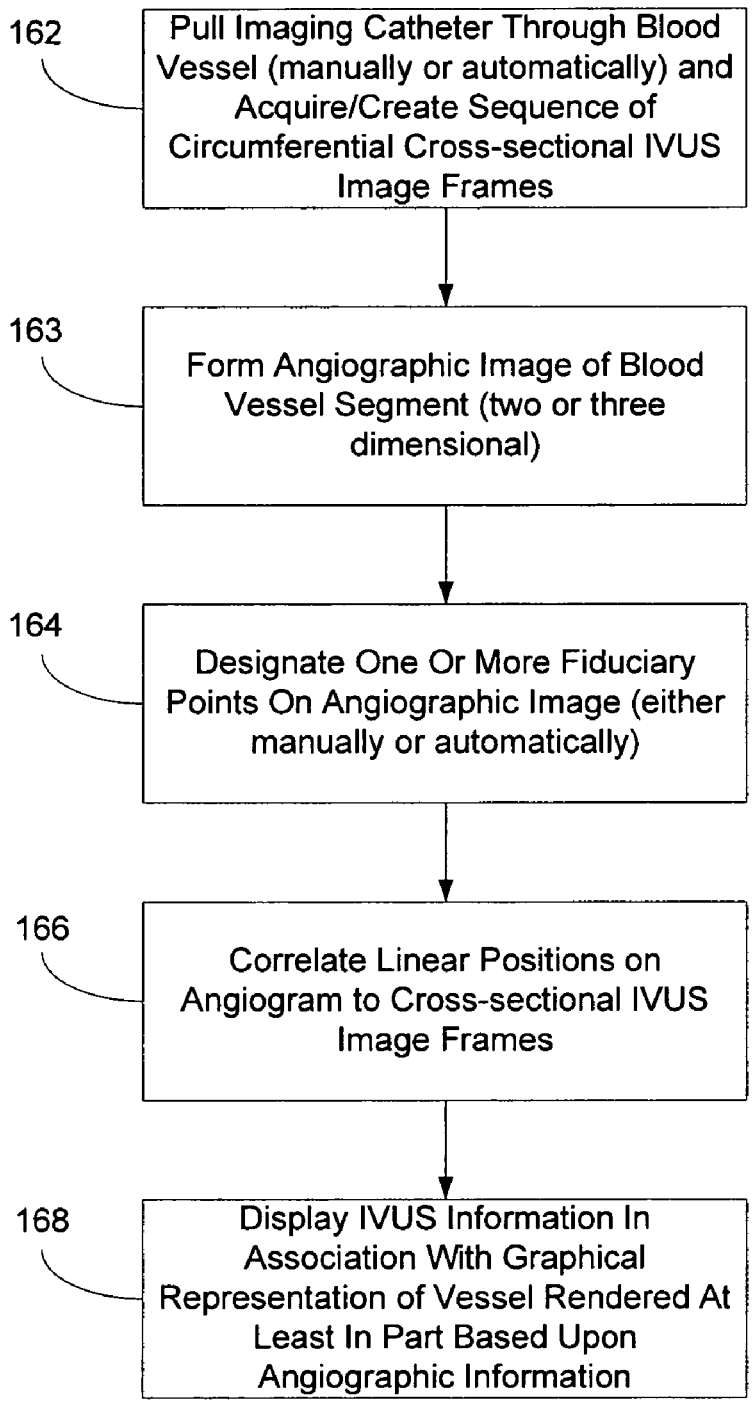
FIG. 6b is a flowchart depicting a set of exemplary steps for creating a co-registered three-dimensional graphical display.

Turning to FIG. 6*b*, a set of steps are depicted for creating a volumetric map. The particular order of the steps differs in alternative embodiments. During step 162, the imaging catheter is pulled back either manually or automatically through a blood vessel segment, and a sequence of circumferential cross-sectional IVUS image frames is acquired/created. During step 163 an angiographic image is formed of the blood vessel segment. The image is, for example, a two-dimensional image or, alternatively a three-dimensional image created from two or more angiographic views. During step 164, at least one fiduciary point is designated on the angiographic image, either by the user, or automatically by the imaging system. During step 166, the angiographic image and the information obtained from the imaging catheter during the pullback are aligned/correlated using the fiduciary point locating information. Thereafter, during step 168 the cross-sectional IVUS images are displayed on a graphical display in association with a two- or three-dimensional graphical representation of the imaged vessel. The graphical representation of the imaged vessel is based at least in-part upon the angiographic image information. By way of example, in an exemplary embodiment, the angiographic image itself is displayed. In an alternative embodiment, information from an angiographic image is only used to guide piece-wise reconstruction of the imaged vessel from the sequence of IVUS image slices by determining the linear displacement and orientation of adjacent sections of the reconstructed vessel using the angiographic image of the vessel.

Turning to FIG. 7, by combining or overlaying the three-dimensional map of imaging information over the three-dimensional image 160 of the vessel lumen, or over one or more two-dimensional views of the angiogram, a reconstruction 165 that more realistically represents the actual vessel is obtained, which is correct in its portrayal of vessel tortuosity, plaque composition and associated location and distribution in three dimensions. For example, a necrotic core which is located in the vessel in the sector between 30° to 90°, also having a certain amount of longitudinal depth, will appear on the reconstruction 165 with the same geometry. An augmented overall vessel diameter, due to thickened plaque, will also appear this way in the reconstruction 165. The additional information from the non-angiography imaging data makes displaying such vessel images possible. The steps of the procedure summarized in FIG. 6*a* facilitate co-registration of the IVUS information over a live two-dimensional angiographic image, giving the operator the ability to view a projection of the volume of plaque over a two-dimensional image of the lumen. The co-registered displayed graphical image allows an operator to make a more informed diagnosis, and also allows the operator to proceed with therapeutic intervention with the additional information provided by the co-registered displayed image guiding the intervention.

In the case of live two-dimensional or three-dimensional co-registration, one or more fiduciary points are selected first, followed by alignment by the system, and then simultaneous pullback and angiography or fluoroscopy. Note that in both co-registration in playback mode and co-registration in "live" mode, the information used by the system includes both the specific pullback speed being used (for example 0.5 millimeters per second) and the time vector of the individual image frames (for example IVUS image frames). This information tells the system where exactly the imaging element is located longitudinally when the image frame is (or was) acquired, and allows for the creation of an accurate longitudinal map.

Automatic fiduciary points are used, for example, and are automatically selected by the system in any one of multiple potential methods. A radiopaque marker on the catheter, approximating the location of the imaging element, for example is identified by the angiography system, creating the fiduciary point. Alternatively, the catheter has an electrode, which is identified by three orthogonal pairs of external sensors whose relative locations are known. By measuring field strength of an electrical field generated by the probe, the location of the electrode is "triangulated".

FIG. 7 graphically depicts a reconstruction produced using the techniques discussed above. Three necrotic cores 80*a*, 80*b* and 80*c* have been identified. First necrotic core 80*a* is located at twelve o'clock circumferentially in the vessel and is identified as being located in the stenosis 60, and deep beneath a thickened cap. The location of the necrotic core 80*a* beneath the thickened cap suggests that this necrotic core is more stable than the other two necrotic cores—core 80*b* which is very close to the surface, and 80*c* which is also close to the surface. As shown in this reconstruction, and in relation to the first necrotic core 80*a*, the second necrotic core 80*b* is located at nine o'clock and the third necrotic core 80*c* is circumferentially located at four o'clock. This circumferential information is employed, for example, to localize application of appropriate treatment. The graphically depicted information provided by the imaging catheter and reconstruction allows delivery of the therapeutic catheter to the precise treatment location, with the desired catheter orientation. Alternatively, the imaging catheter itself is a combination imaging and therapy catheter, and the treatment simultaneously coincides with the imaging. One possible treatment scenario involves placing a drug eluting stent at the portion of the depicted vessel near the stenosis 60 and treating the second and third necrotic cores 80*b* and 80*c* by a needle-based drug, cell (i.e. stem cell) or gene delivery catheter (U.S. Pat. No. 6,860,867 to Seward), or by removing the necrotic core material by a needle and vacuum catheter. If using a tissue removal technique, such as atherectomy, ultrasonic therapeutics, or a plaque modification technique such as photodynamic therapy, drug delivery, radiation, cryoplasty, radiofrequency heating, microwave heating or other types of heating, the knowledge of the location of the EEL 50 is important. This assures that the adventitia is not disturbed, and that vessel perforation does not occur. The reconstruction 165 is graphically displayed in a manner that clearly demonstrates the location of the EEL 50 from all viewing angles. It can be seen that the thickness 170 between the luminal boundary and the EEL 50 at the stenosis 60 is much larger than the thickness 175 between the luminal boundary and the EEL 50 proximal to the stenosis 60. The circumferential (azimuthal) and radial (depth) orientation of the plaque components has been discussed herein above, but the axial (longitudinal) orientation/positioning—the distances separating diseased sections along a vessel's length—is important also. First necrotic core 80*a* is further distal than second necrotic core 80*b*, and second necrotic core 80*b* is further distal than third necrotic core 80*c*. The axial arrangement (lengthwise positioning) of diseased sections is important when choosing a particular length of a stent to use, or where to place the distal-most or proximal-most portion of the stent. It is also important when determining the order or operation in the treatment sequence. In addition, very proximally located vulnerable plaques are generally of greater concern than distally located vulnerable plaques, because they supply blood to a larger volume of myocardium.

Arteries also have side branches which can be identified with imaging techniques such as standard IVUS imaging, or IVUS flow imaging (which identifies the dynamic element of blood). The side branches are potentially used as fiduciary points for axial, circumferential and even radial orientation of the IVUS information, with respect to an angiographic base image, which also contains side branch information.

Turning to FIGS. 14-20, an exemplary technique is illustrated for obtaining accurate axial and circumferential co-registration of IVUS information (or other image information obtained via a probe inserted within a body) with the three-dimensional image 160. Turning initially to FIG. 14 and FIG. 15, the illustrations are intended to represent the internal representation of information created/processed by the imaging/display system. However, in an illustrative embodiment, such information is presented as well as graphical displays rendered by the system, in the manner depicted in FIGS. 14 and 15 as a visual aid to users in a semi-automated environment. For example, a user can manually move the relative positioning of a sequence of IVUS frames with regard to linear displacement of a vessel as depicted in corresponding data values generated from an angiographic image.

Furthermore, as those skilled in the art will readily appreciate, the line graphs in FIGS. 14 and 15 corresponding to IVUS frames comprise a sequentially ordered set of discrete values corresponding to a sequence of "N" frames of interest. Similarly, values generated from angiographic image data are also taken at discrete points along a length of a vessel of interest. Thus, while depicted as continuous lines in the drawing figures, the values calculated from angiographic and IVUS information correspond to discrete points along the length of the vessel.

FIG. 14 includes a graph 320 depicting calculated/estimated lumen area as a function of IVUS image frame number for both angiography and IVUS. The graph depicted in FIG. 14 shows the effect of inaccurate co-registration between two imaging methods and associated measured parameters (e.g., lumen cross-section size). A line graph 330 representing lumen area calculated from IVUS information and a line graph 325 representing lumen area calculated from angiography information are shown in an exemplary case wherein the measurements are misaligned along a portion of a vessel.

FIG. 14 corresponds to a graphically displayed composite image depicted in FIG. 16 that includes a graphical representation of a three-dimensional angiographic image 335 and a graphical representation of corresponding IVUS information 340 where the two graphical representations are shifted by a distance ("D") in a composite displayed image. The misalignment is especially evident because minimum luminal circumferential cross-section regions (i.e., the portion of the vessel having the smallest cross-section) in the images graphically rendered from each of the two data sets do not line up. The minimal lumen area calculated from the IVUS information at point 345 in FIG. 14 corresponds to the IVUS minimal lumen position 360 in FIG. 16. The lumen area calculated from the angiography information at point 350 in FIG. 14 corresponds to the angiography minimal lumen position 355 in FIG. 16. Note that in the illustrative example, thickness of the vessel wall is depicted as substantially uniform on IVUS. Thus, an IVUS image frame where the minimal lumen area occurs is also where the minimum vessel diameter exists. This image feature differs from restricted flow due to a blockage within a diseased artery such as the one depicted in FIG. 2.

A lumen border 380 is also shown in FIG. 16. In order to achieve axial alignment between the graphical representation of the three-dimensional angiographic image 335 and the graphical representation of corresponding IVUS information 340, an axial translation algorithm is obtained based upon a "best-fit" approach that minimizes the sum of the squared differences between luminal areas calculated using the angiographic and the IVUS image data.

The best axial fit for establishing co-registration between angiogram and IVUS data is obtained where the following function is a minimum.

$$\sum_{n=1}^{N} (A_{Lumen} - A_{Angio})^2;$$

with $A_{Lumen}$=IVUS lumen area for frames n=1, N and $A_{Angio}$=angiography area for "frames" n=1, N (sections 1-N along the length of an angiographic image of a blood vessel). By modifying how particular portions of the angiographic image are selected, the best fit algorithm can perform both "skewing" (shifting all slices a same distance) and "warping" (modifying distances between adjacent samples).

Figure 17:
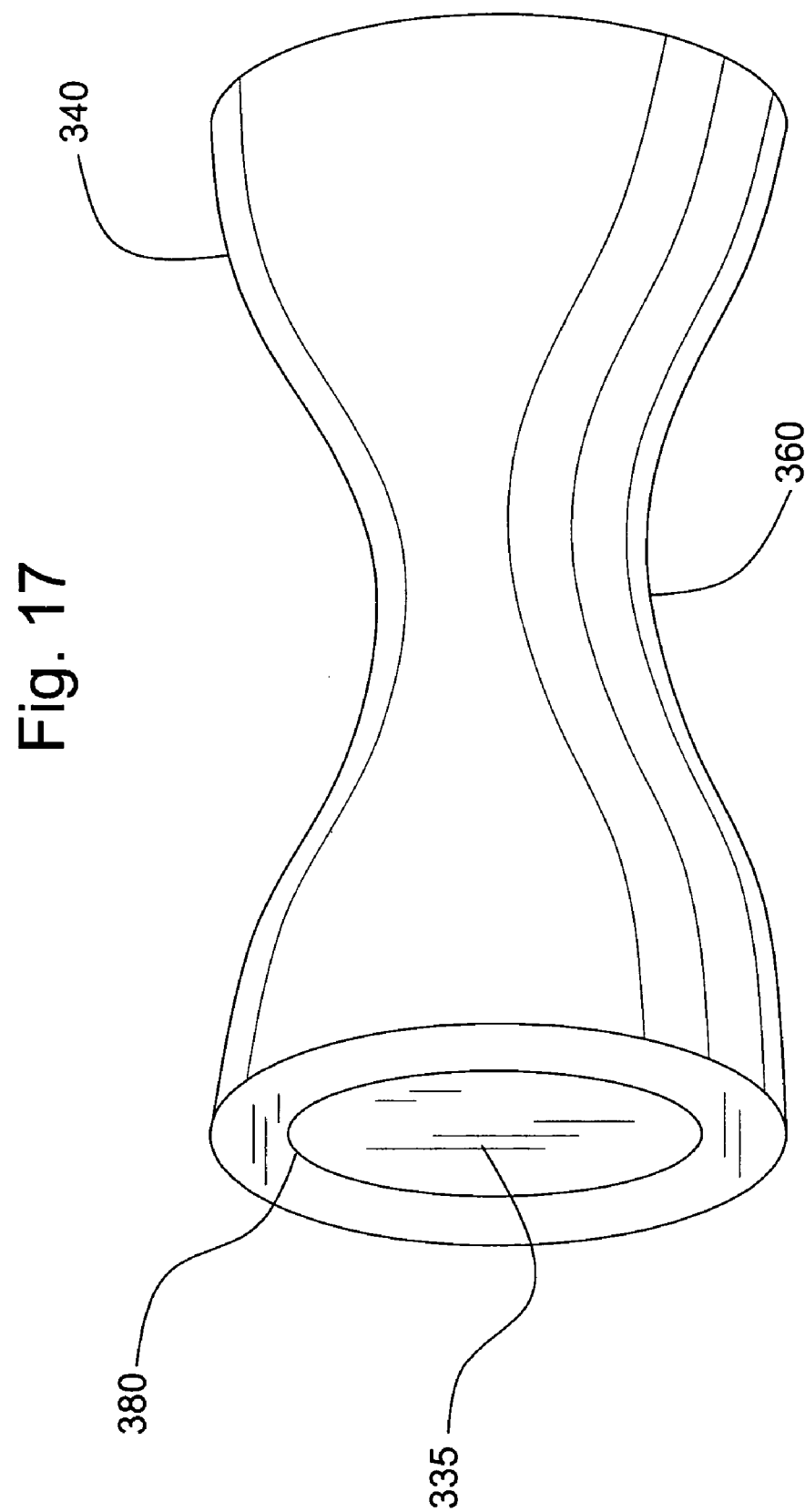
FIG. 17 illustratively depicts a graphical display of angiography and vessel (e.g., IVUS) images superimposed on a single graphical display after axial registration adjustment.
Figure 18:
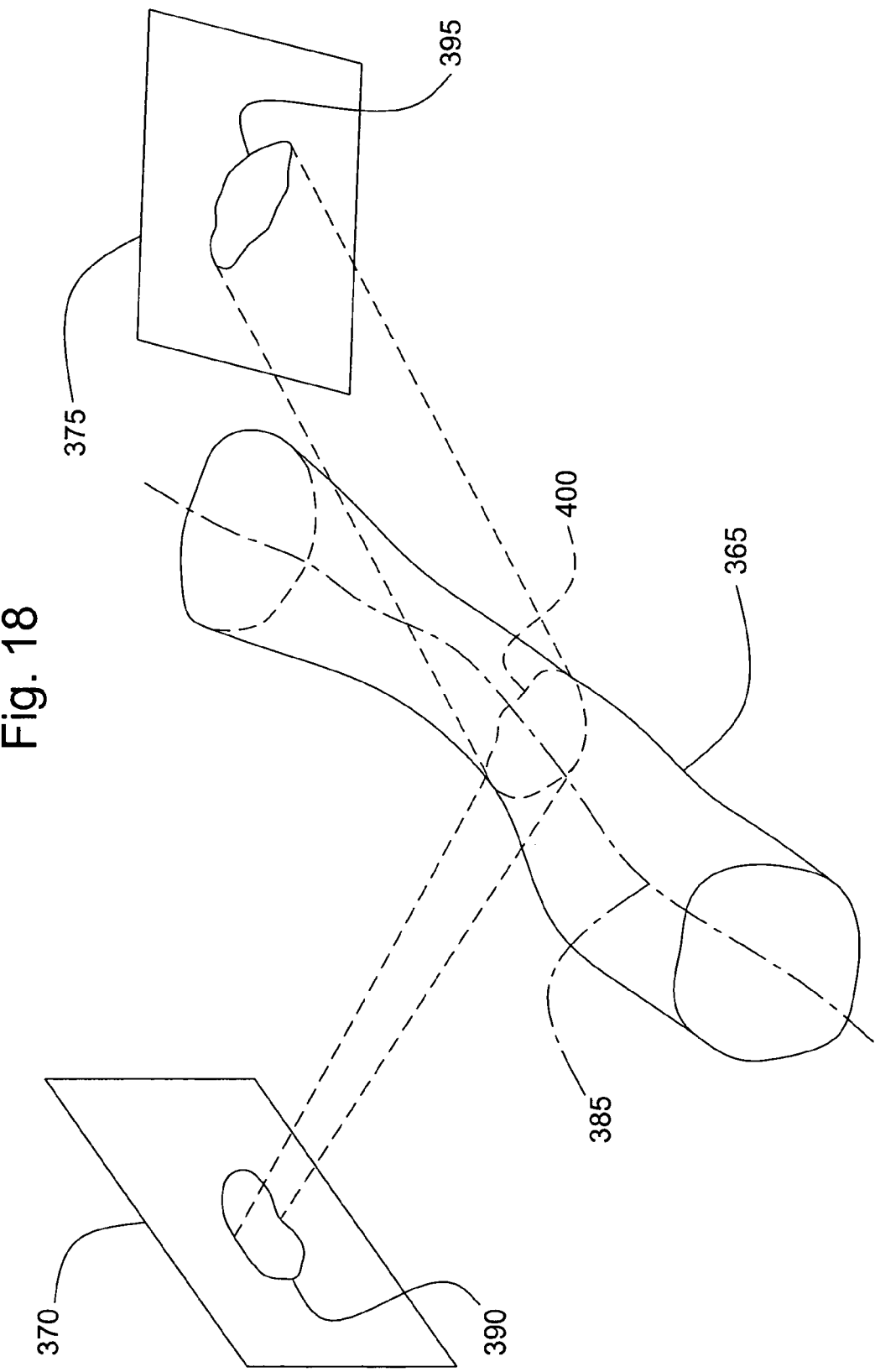
FIG. 18 illustratively depicts the process of circumferential registration of angiography and vessel (e.g., IVUS) image sets.

Using the axial alignment of frames where the summation function is a minimum, a desired best fit is obtained. FIGS. 15 and 17 depict a result achieved by realignment of line graphs and corresponding graphical representations generated from the angiographic and IVUS data, depicted in a pre-aligned state in FIGS. 14 and 16, based upon application of a "best fit" operation on frames of IVUS image data and segments of a corresponding angiographic image, FIG. 18 illustratively depicts a graphical representation of a three-dimensional lumen border 365 rendered from a sequence of IVUS image slices after axially aligning a three-dimensional angiographic data-based image with a graphical image generated from IVUS information for a particular image slice. The displayed graphical representation of a three dimensional image corresponds to the lumen border 380 shown in FIG. 17. The lumen border 380 is shown projected over a three-dimensional center line 385 obtained from the angiographic information. FIG. 18 also depicts a first angiography image plane 370 and a second angiography image plane 375 that are used to construct the three dimensional center line 385 and three-dimensional angiographic image 335. Such three-dimensional reconstruction is accomplished in any one of a variety of currently known methods. In order to optimize the circumferential orientation of each IVUS frame, an IVUS frame 400 depicting a luminal border is projected against the first angiography plane 370, where it is compared to a first two-dimensional angiographic projection 390. In addition, or alternatively, the IVUS frame 400 is projected against the second angiography image plane 375, where it is compared to the second two-dimensional angiographic projection 395 for fit. Such comparisons are carried out in any of a variety of ways including: human observation as well as automated methods for comparing lumen cross section images (e.g., maximizing overlap between IVUS and angiogram-based cross-sections of a vessel's lumen).

Figure 19:
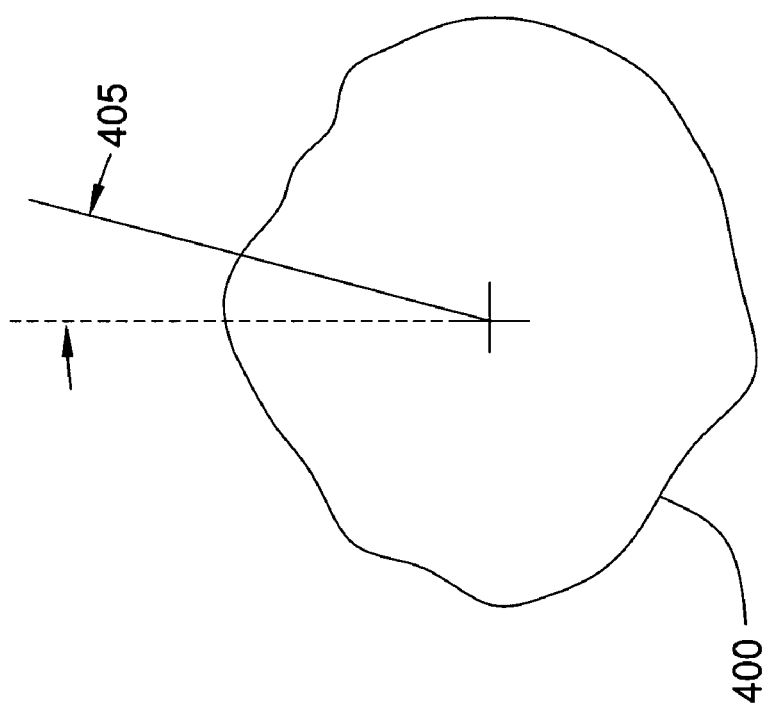
FIG. 19 illustratively depicts angular image displacement in relation to circumferential registration of angiography and vessel (e.g., IVUS) image sets.

Positioning an IVUS frame on a proper segment of a graphical representation of a three-dimensional angiographic image also involves ensuring proper circumferential (rotational) alignment of IVUS slices and corresponding sections of an angiographic image. Turning to FIG. 19, after determining a best axial alignment between an IVUS image frame, such as frame 400, and a corresponding section of a three-dimensional angiographic image, the IVUS frame 400 is then rotated in the model by an angular displacement 405 (for example 1°), and the fit against the angiographic projections is recalculated. As mentioned above, either human or automated comparisons are potentially used to determine the angular displacement. After this has been done over a range of angular orientations, the best fit angular rotation is determined.

Figure 20:
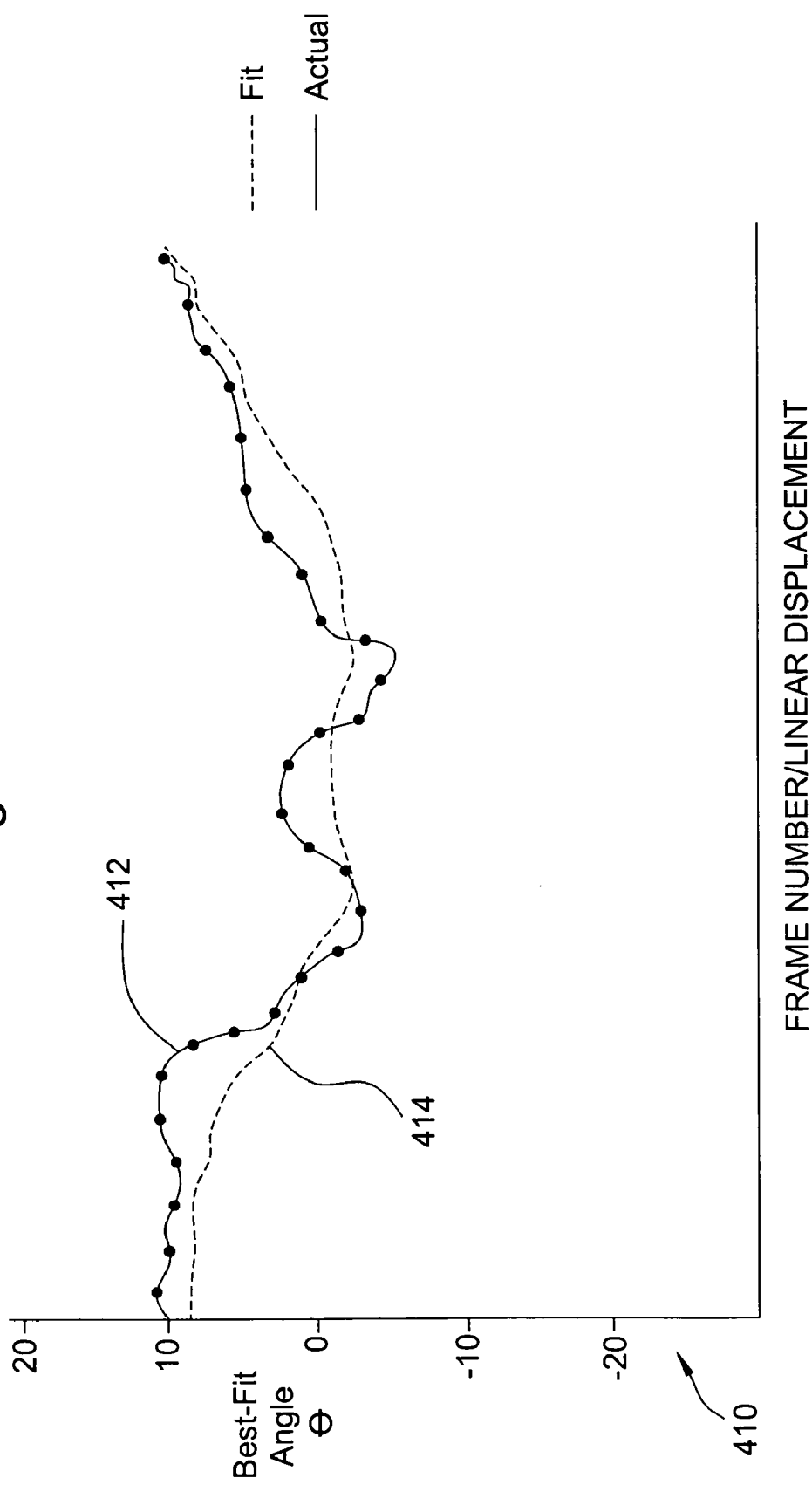
FIG. 20 illustratively depicts a graph of actual and best fit rotational angle corrections displayed in relation to image frame number.

FIG. 20 depicts a graph 410 of best angle fit and frame number. During the pullback of the IVUS catheter, there may be some slight rotation of the catheter, in relation to the centerline of the blood vessel, and so, calculating the best angular fit for one IVUS frame does not necessarily calculate the best fit for all frames. The best angular fit is done for several or all frames in order to create the graph 410 including actual line 412 and fit line 414. The actual line 412 comprises a set of raw angular rotation values when comparing IVUS and angiographic circumferential cross-section images. The fit line 414 is rendered by applying a limit on the amount of angular rotation differences between adjacent frame slices (taking into consideration the physical constraints of the catheter upon which the IVUS imaging probe is mounted). By way of example, when generating the fit line 414, the amount of twisting between frames is constrained by fitting a spline or a cubic polynomial to the plot on the actual line 412 in graph 410.

Having described an illustrative way to co-register angiographic and IVUS images for graphically representing a three-dimensional image of a vessel, attention is directed to FIGS. 8a, 8b and 8c that demonstrate the use of a directional atherectomy catheter 180 using guidance from the reconstruction 165. The directional atherectomy catheter 180 has a tapered receptacle tip 190 and a cutter window 185. In use, the catheter is manipulated, using a balloon or an articulation, to force the cutter window 185 against the atherosclerotic plaque so that the plaque protrudes into the cutter window 185. The plaque is then sliced off by a cutter (not shown) and collected in the tapered receptacle tip 190. In order to debulk the artery as much as possible (remove the plaque) it is desirable to cut away the plaque up to, but not past the EEL 50. The reconstruction 165 is used as a guide to track the directional atherectomy catheter 180 into a desired axial location along the length of the vessel. Thereafter, the catheter 180 is "torqued" (rotated at least partially) until the cutter window 185 is in the desired circumferential orientation. One in position the balloon or articulation is activated until the cutter window 185 is set up to allow the cutting of desired plaque but not adventitial tissue. In other words, only tissue within the EEL 50 boundary is excised.

With continued reference to FIG. 8a, using the reconstructed co-registered angiographic and IVUS images as a guide for the procedure, the directional atherectomy catheter 180 is tracked into place and torqued opposite an upper portion 60a of the stenosis. In FIG. 8b, an appropriate catheter mechanism, such as a balloon (not shown) is activated to force the cutting window 185 against an upper portion 60a of the stenosis. The upper portion 60a of the stenosis is then excised. During this cutting operation, the reconstruction procedure that achieves co-registration of the angiographic and IVUS images on a graphical three-dimensional rendering of a vessel allows the user to be fully aware of the location of the EEL 50, and thus the user knows when to stop articulating and cutting. FIG. 8c shows a directional atherectomy catheter 180 being tracked, torqued and articulated so that it can cut a lower portion 60b of the stenosis, again using a co-registered IVUS cross-sectional image to avoid cutting past the EEL 50 and into the adventitia 55. This is especially useful in debulking areas of large plaque volume, such as in the arteries of the leg (femoral, popliteal). The debulking is performed using the vessel visualization apparatus and methods described herein that are based upon use of both angiographic and IVUS image data. Debulking or other therapies may also be done using this smart visualization, and in combination with automated or semi-automated robotic or magnetic catheter manipulation systems.

Turning to FIG. 9, a dilatation balloon catheter 195 is prepared based on information derived from the reconstruction 165 of FIG. 7. A first stent 200a, second stent 200b and third stent 200c are crimped onto the dilatation balloon catheter 195 or attached by other methods known in the art. The first stent 200a is configured to correspond with stenosis 60. The stent is made from a mesh that has a higher metal to artery ratio than the other stents, to prevent distal embolization from unorganized thrombus which may occur near the flap 65. The stent may or may not be drug eluting. For example, if the artery is 3.5 mm or larger, a drug eluting stent is not always necessary to prevent restenosis. However, most fiberatheromas will necessitate a drug eluting stent to prevent in-stent restenosis. Because the first necrotic core 80a is deep within the stenosis, the stent serves more as a mechanical support for the entire dilated stenosis, rather than protection against rupture of this portion of the blood vessel. In contrast, necrotic cores 80b and 80c are closer to the lumen of the vessel and need to be treated in a more urgent manner. Second stent 200b is configured to be expanded over the second necrotic core 80b. A biodegradable stent (such as magnesium or a polymeric material) may be chosen, because it will be expanded in an area that does not require a high radial force to keep the artery open (this is already a non-stenotic area). The stent is designed to elute a statin, and the statin is more heavily dosed at the nine o'clock portion (not shown in FIG. 9) that corresponds with the second necrotic core 80b. The third stent 200c is the same as the second stent, 200b, except that it is oriented on the catheter with the more heavily dosed area 230 at four o'clock, in order to correspond with the third necrotic core 80c. By more properly dosing the drugs on the stents, there is less risk of wasted drug from high doses, being leaked systemically into a patient's body, and potentially causing harmful side effects. Not shown in this figure is another stent configuration that has a side hole that allows the stent to be placed over a sidebranch without obstructing flow of blood to the sidebranch. The image co-registration reconstruction method and apparatus described herein is also capable of identifying the size, location and orientation of sidebranches, and can be used to orient (circumferentially, axially) a side-hole stent of this design.

The catheter in FIG. 9 has four radiopaque markers 205a-205d, which delineate the positions of the three different short stents 200a, 200b and 200c. The catheter also has radiopaque markings or stripes that allow its circumferential orientation to be visible on X-ray. For example, a radiopaque marker band that does not completely encircle the catheter, so that visible portions and non-visible portions can be identified around the circumference of the marker.

FIG. 10 shows an overlay 235 of the reconstruction 165 placed over the live angiography image 240. As a catheter is tracked through the vessel, the atherosclerotic plaque 225 and the EEL 220 is identified. In combination with tissue characterization and colorization, structures of concern 245 are easily identified in relation to the live image 240. Sidebranches 250 are used, for example, to align and co-register the two different images. Combining the three-dimensional reconstruction with tissue characterization information and a live two-dimensional angiography image, facilitate tracking and manipulating a therapeutic catheter (not shown) to areas that are of primary concern. It also allows for a more informed awareness of the state of vulnerability of various regions of the vessel. In the stenosis, target plaque 255 is viewed against a live two-dimensional angiography image to better aid plaque removal techniques, such as directional atherectomy.

FIGS. 11, 12 and 13 illustratively depict three different graphic displays for graphically representing information relating to plaque size and composition. A vessel lumen trace 260 is, for example, either a three-dimensional rendering of the vessel lumen (for example derived from two two-dimensional angiography images) or a two-dimensional projection of the three dimensional rendering. Alternatively, vessel lumen trace 260 is represented by a live angiographic image. In all of the aforementioned alternative angiographic imaging modes, it is possible to overlay images of the atherosclerotic plaque, however, it is difficult to appreciate the thickness, contours and composition of the plaque at all points extending circumferentially around the vessel by simply looking at a single projection.

FIG. 11 is a graphical image representation that embodies a technique that utilizes information calculated from IVUS imaging (or other imaging) and places a maximum thickness line 265 and a minimum thickness line 270 above and below the trace. Though not specific of where, circumferentially, the thickest portion of plaque occurs, the maximum thickness line 265 shows the exact maximum thickness of the plaque at each longitudinal position along the artery. In other words, a curving, continuous central axis parameter 275 follows the centerline of the artery and represents the axial location of the plaque, while a perpendicular axis parameter 280 represents the maximum thickness of the plaque by its distance from the edge of the vessel lumen trace 260. In a similar manner, the minimum thickness line 270 represents the minimum thickness of the plaque in the negative direction. It can be appreciated immediately while viewing the image/graphic combination depicted in FIG. 11 that the plaque is eccentric at various sections, even though there is no information present in this image/graphic combination to identify the exact circumferential angle where the maximum plaque thickness occurs. By viewing this image/graphic combination, the operator can immediately focus on the areas where the plaque is more eccentric, and the operator can also get a measurement of the minimum and maximum plaque thickness.

FIG. 12 illustratively depicts a graphical technique similar to that of FIG. 11, but with more specific information, namely the volume of plaque composition over a chosen length of vessel. A bar graph 285 is placed along-side the vessel lumen trace 260, and represents the volume of the different plaque components over a length of vessel. The user picks the proximal and distal point on the vessel which define a region of interest (for example a possible area of vulnerability), and the data obtained in this area is displayed with the bar graph 285. The bar graph 285 in this case represents four plaque components, fibrous 290, fibro-fatty 295, necrotic core 300, and dense calcium 305. The thickness (height in the radial direction) of each individual bar is proportional to the volume of that plaque component measured in a visually designated/indicated length of vessel. Each bar is color coded with a characteristic color to allow easier visual identification. For example, fibrous—dark green, fibrofatty—light green, necrotic core—red, dense calcium—white.

FIG. 13 illustratively depicts a graphical technique that is very similar to the one described in FIG. 11; however, instead of describing maximum and minimum plaque thickness at each axial location, the actual plaque thickness at each of the two sides is graphed. When the vessel lumen trace 260 is displayed in a two-dimensional mode, the upper thickness line 310 and the lower thickness line 315 graph the thickness of the plaque at points 180° from each other (for example at twelve o'clock and six o'clock), depending on the orientation chosen for the vessel lumen trace 260.

The invention described herein is not limited to intravascular applications or even intraluminal applications. Tissue characterization is also possible in cancer diagnostics, and it is conceivable that a probe that images for cancer can also be used in conjunction with a three-dimensional map to create a similar reconstruction as that described above. This can be used to guide biopsy or removal techniques. Such cancers include, but are not limited to: prostate, ovarian, lung, colon and breast. In the intravascular applications, both arterial and venous imaging is conceived. Arteries of interest include, by way of example: coronaries, carotids, superficial femoral, common femoral, iliac, renal, cerebral and other peripheral and non-peripheral arteries.

The intravascular ultrasound methods described can also be expected to be applicable for other ultrasound applications, such as intracardiac echocardiography (ICE) or transesophageal echocardiography (TEE). Therapeutic techniques that are guided by these techniques include, but are not limited to, patent foramen ovale closure, atrial septal defect closure, ventricular septal defect closure, left atrial appendage occlusion, cardiac biopsy, valvuloplasty, percutaneous valve placement, trans-septal puncture, atrial fibrillation ablation (of pulmonary veins or left atrium, for example) and TIPS (transjugular intrahepatic portosystemic shunt for pulmonary hypertension).

Similar to the selective use of directional atherectomy and stenting/drugs in the circumferential, radial and axial orientations, the other energy delivery methods can also be manipulated as such. For example, in a thicker plaque, a higher power can be used in a cryogenic cooling catheter, etc. In addition, image guided automatic feedback can be used to automatically determine when to apply energy and when to stop applying energy, based on the information in the reconstruction. This is particularly of use in radiofrequency ablation of pulmonary veins for treatment of atrial fibrillation.

All of the image guided therapy described in this invention, can be conceived to be a combination of imaging and therapy on the same catheter, or to be two or more different catheters, each specialized in its use.

All of the techniques described here can also be used in conjunction with external imaging technologies such as MRI, CT, X-ray/angiography and ultrasound. Three dimensional reconstructions, for example from CT or MRI, can be co-registered with the imaging information in the same way as angiography.

The three-dimensional mapping of imaging information can also be combined with a three dimensional mapping of the electrical activity of the heart, for example, from information obtained from catheter-based electrodes. This is of use in a patient that has had an acute myocardial infarction.

It is also conceivable to include three-dimensional fluid mechanics analysis in the reconstruction so that points of high stress are identified.

The structures, techniques, and benefits discussed above, for illustrative systems embodying the present invention, are exemplary. In view of the many possible embodiments to which the principles of this invention may be applied, it should be recognized that the embodiments described herein with respect to the drawing figures are meant to be illustrative only and should not be taken as limiting the scope of the invention. Therefore, the invention as described herein contemplates all such embodiments as may come within the scope of the following claims and equivalents thereof.

What is claimed is:

1. A method, comprising:
    obtaining angiographic image data of a vessel segment from an imaging device positioned external to the vessel segment;
    creating a three-dimensional image of the vessel segment based upon the obtained angiographic image data;
    obtaining intravascular ultrasound (IVUS) image data of the vessel segment from an imaging device positioned within the vessel segment, wherein the IVUS image data comprises a series of intravascular images acquired as the imaging device positioned within the vessel segment is moved through and along the vessel segment;
    correlating IVUS image data to the three-dimensional image of the vessel such that each of the images of the series of intravascular images of the IVUS image data is correlated to a portion of the three-dimensional image of the vessel created based upon the obtained angiographic image data, wherein correlating the IVUS image data to the three-dimensional image of the vessel includes aligning the images of the series of intravascular images of the IVUS image data both axially and circumferentially to the corresponding portions of the three-dimensional image of the vessel, wherein the images of the series of intravascular images of the IVUS image data are axially aligned with the three-dimensional image of the vessel by determining a best axial fit between a lumen measurement of the vessel segment as depicted in the images of the series of intravascular images of the IVUS image data and a lumen measurement of the vessel segment as depicted in the three-dimensional image of the vessel segment based on the obtained angiographic image data, and wherein the images of the series of intravascular images of the IVUS image data are circumferentially aligned with the three-dimensional image of the vessel after the images of the series of intravascular images of the IVUS image data are axially aligned with the three-dimensional image of the vessel and wherein the images of the series of intravascular images of the IVUS image data are circumferentially aligned with the three-dimensional image of the vessel by determining a best angular fit between a lumen measurement of the vessel segment as depicted in the images of the series of intravascular images of the IVUS image data and a lumen measurement of the vessel segment as depicted in the three-dimensional image of the vessel segment based on the obtained angiographic image data;
    rendering simultaneously on a display an image of the series of intravascular images of the IVUS image data and at least the correlated portion of the three-dimensional image of the vessel as determined by the correlating step;
    wherein the lumen measurement is a cross-sectional area; and
    wherein determining the best axial fit between the cross-sectional area of the vessel segment as depicted in the images of the series of intravascular images of the IVUS image data and the cross-sectional area of the vessel segment as depicted in the three-dimensional image of the vessel segment based on the obtained angiographic image data comprises determining a minimum of the sum of the squared differences between the cross-sectional area of the vessel segment as depicted in the images of the series of intravascular images of the IVUS image data and the cross-sectional area of the vessel segment as depicted in the three-dimensional image of the vessel segment based on the obtained angiographic image data.

2. The method of claim 1, wherein time vectors of the series of intravascular images and a pullback speed of the imaging device are utilized to axially align the images of the series of intravascular images of the IVUS image data with the three-dimensional image of the vessel.

3. The method of claim 1, wherein determining the best axial fit between the cross-sectional area of the vessel segment as depicted in the images of the series of intravascular images of the IVUS image data and the cross-sectional area of the vessel segment as depicted in the three-dimensional image of the vessel segment based on the obtained angiographic image data comprises determining a minimum of $$\sum_{n=1}^{N} (A_{IVUS} - A_{Angio})^2,$$

where $A_{IVUS}$ is the cross-sectional area of the vessel as depicted in images 1 to N of the series of intravascular images of the IVUS image data and $A_{Angio}$ is the cross-sectional area of the vessel as depicted in the three-dimensional image of the vessel segment based on the obtained angiographic image.

4. The method of claim 1, wherein axially aligning the images of the series of intravascular images of the IVUS image data with the three-dimensional image of the vessel includes applying a skewing displacement.

5. The method of claim 1, wherein axially aligning the images of the series of intravascular images of the IVUS image data with the three-dimensional image of the vessel includes applying a warping displacement.

6. The method of claim 1, wherein circumferentially aligning the images of the series of intravascular images of the IVUS image data with the three-dimensional image of the vessel includes rotating the images of the series of intravascular images of the IVUS image data based on a best angular fit.

7. The method of claim 6, wherein the best angular fit is determined for a plurality of the images of the series of intravascular images of the IVUS image data.

8. The method of claim 6, wherein the best angular fit is determined for each of the images of the series of intravascular images of the IVUS image data.

9. The method of claim 6, wherein a degree of rotation between adjacent images of the series of intravascular images of the IVUS image data is limited.

10. The method of claim 9, wherein the degree of rotation between adjacent images of the series of intravascular images of the IVUS image data is limited by a spline fit.

11. The method of claim 9, wherein the degree of rotation between adjacent images of the series of intravascular images of the IVUS image data is limited by a cubic polynomial fit.

12. The method of claim 1, wherein each of the images of the series of intravascular images of the IVUS image data is correlated to a portion of the three-dimensional image of the vessel created based upon the obtained angiographic image data in a live mode.

13. The method of claim 12, wherein the angiographic image data and the IVUS image data are obtained simultaneously.

14. The method of claim 1, wherein each of the images of the series of intravascular images of the IVUS image data is correlated to a portion of the three-dimensional image of the vessel created based upon the obtained angiographic image data in a playback mode.

15. The method of claim 14, wherein the angiographic image data and the IVUS image data are obtained simultaneously.

16. The method of claim 1, wherein the angiographic image data and the IVUS image data are obtained simultaneously.

17. The method of claim 16, further comprising aligning the imaging device positioned external to the vessel segment with the imaging device positioned within the vessel segment using at least one fiduciary point.

18. The method of claim 17, wherein the at least one fiduciary point is a marker associated with the imaging device positioned within the vessel segment.

19. The method of claim 18, wherein the marker is a radiopaque marker.

20. The method of claim 18, wherein the marker is an electrode.

21. The method of claim 1, further comprising treating a portion of the vessel using the simultaneously rendered image of the series of intravascular images of the IVUS image data and at least the correlated portion of the three-dimensional image of the vessel for visual guidance.

22. The method of claim 21, wherein treating the portion of the vessel comprises placing a stent.

23. The method of claim 1, wherein the step of rendering simultaneously on a display an image of the series of intravascular images of the IVUS image data and at least the correlated portion of the three-dimensional image of the vessel as determined by the correlating step includes overlaying the image of the series of intravascular images of the IVUS image data onto the correlated portion of the three-dimensional image of the vessel.

24. The method of claim 1, wherein the step of rendering simultaneously on a display an image of the series of intravascular images of the IVUS image data and at least the correlated portion of the three-dimensional image of the vessel as determined by the correlating step includes displaying a maximum thickness line and a minimum thickness line on the three-dimensional image of the vessel based on the IVUS image data.

25. A method, comprising:
obtaining angiographic image data of a vessel segment from an imaging device positioned external to the vessel segment;
obtaining intravascular ultrasound (IVUS) image data of the vessel segment from an imaging device positioned within the vessel segment, wherein the IVUS image data comprises a series of intravascular images acquired as the imaging device positioned within the vessel segment is moved through and along the vessel segment, wherein the IVUS image data is obtained simultaneously with the angiographic image data;
correlating IVUS image data to the angiographic image data of the vessel such that each of the images of the series of intravascular images of the IVUS image data is correlated to a portion of the angiographic image data, wherein correlating the IVUS image data to the angiographic image data includes aligning the images of the series of intravascular images of the IVUS image data both axially and rotationally to corresponding portions of the angiographic image data, wherein the images of the series of intravascular images of the IVUS image data are axially aligned with the three-dimensional image of the vessel by determining a best axial fit between a lumen measurement of the vessel segment as depicted in the images of the series of intravascular images of the IVUS image data and a lumen measurement of the vessel segment as depicted in the angiographic image data, and wherein the images of the series of intravascular images of the IVUS image data are rotationally aligned with the angiographic image data by determining a best angular fit between a lumen measurement of the vessel segment as depicted in the images of the series of intravascular images of the IVUS image data and a lumen measurement of the vessel segment as depicted in the angiographic image data;
displaying simultaneously at least one image of the series of intravascular images of the IVUS image data and at least the correlated portion of the angiographic image data as determined by the correlating step;
wherein the lumen measurement is a cross-sectional area; and
wherein determining the best axial fit between the cross-sectional area of the vessel segment as depicted in the images of the series of intravascular images of the IVUS image data and the cross-sectional area of the vessel segment as depicted in the three-dimensional image of the vessel segment based on the obtained angiographic image data comprises determining a minimum of the sum of the squared differences between the cross-sectional area of the vessel segment as depicted in the images of the series of intravascular images of the IVUS image data and the cross-sectional area of the vessel segment as depicted in the three-dimensional image of the vessel segment based on the obtained angiographic image data.

26. The method of claim 25, wherein the step of obtaining angiographic image data includes obtaining a two-dimensional angiographic image data.

27. The method of claim 25, wherein displaying simultaneously at least one image of the series of intravascular images of the IVUS image data and at least the correlated portion of the angiographic image data as determined by the correlating step includes overlaying the at least one image of the series of intravascular images of the IVUS image data onto the correlated portion of the three-dimensional image of the vessel.

* * * * *